US011597766B2

(12) United States Patent
Zugmaier et al.

(10) Patent No.: US 11,597,766 B2
(45) Date of Patent: Mar. 7, 2023

(54) TREATMENT OF ACUTE LYMPHOBLASTIC LEUKEMIA

(71) Applicant: AMGEN RESEARCH (MUNICH) GMBH, Munich (DE)

(72) Inventors: Gerhard Zugmaier, Munich (DE); Evelyn Degenhard, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 658 days.

(21) Appl. No.: 16/218,797

(22) Filed: Dec. 13, 2018

(65) Prior Publication Data

US 2019/0300609 A1 Oct. 3, 2019

Related U.S. Application Data

(63) Continuation of application No. 13/127,541, filed as application No. PCT/EP2009/007970 on Nov. 6, 2009, now abandoned.

(60) Provisional application No. 61/183,291, filed on Jun. 2, 2009, provisional application No. 61/112,323, filed on Nov. 7, 2008.

(51) Int. Cl.
C07K 16/28 (2006.01)
C07K 16/46 (2006.01)

(52) U.S. Cl.
CPC ...... C07K 16/2809 (2013.01); C07K 16/2803 (2013.01); C07K 16/468 (2013.01)

(58) Field of Classification Search
None
See application file for complete search history.

(56) References Cited

U.S. PATENT DOCUMENTS

| 8,338,466 | B2 | 12/2012 | Kunzer et al. | |
|---|---|---|---|---|
| 8,426,422 | B2 | 4/2013 | Hexamer et al. | |
| 8,486,933 | B2 | 7/2013 | Wang et al. | |
| 8,513,243 | B2 | 8/2013 | Zhang et al. | |
| 8,524,867 | B2 | 9/2013 | Bernett et al. | |
| 8,840,888 | B2 * | 9/2014 | Nagorsen | C07K 16/2803 424/136.1 |
| 10,662,243 | B2 * | 5/2020 | Nagorsen | C07K 16/2809 |

FOREIGN PATENT DOCUMENTS

| WO | WO-1998/008875 | | 3/1998 |
|---|---|---|---|
| WO | WO-2005/040220 | A1 | 5/2005 |
| WO | WO-2007/068354 | A1 | 6/2007 |

OTHER PUBLICATIONS

Anderson et al., G19.4(alpha CD3) x B43(alpha CD19) monoclonal antibody heteroconjugate triggers CD19 antigen-specific lysis of t(4;11) acute lymphoblastic leukemia cells by activated CD3 antigen-positive cytotoxic T cells, *Blood.* 80:2826-34 (1992).
Anonymous: "Phase II Study of the BiTE Blinatumomab (MT103) in Patients with Minimal Residual Disease of B-Precursor Acute ALL" retrieved on Mar. 10, 2010 from the Internet: URL:http://clinicaltrials.gov/archive/NCT0_0560794/2008_08_11., Aug. 8, 2008.
Bader et al., Prognostic value of minimal residual disease quantification before allogeneic stem-cell transplantation in relapsed childhood acute lymphoblastic leukemia: the ALL-REZ BFM Study Group, *J. Clin. Oncol.* 27:377-84 (2009).
Bargou et al., The Anti-CD19 Bispecific T-Cell Engager (BiTE) MT103 (MEDI-538), Induces Dose-Dependent Complete and Partial Responses in Relapsed Non-Hodgkin Lymphoma (NHL): Phase I Study MT103-104, *Blood.* 110:2557 (2007).
Bargou et al., Tumor regression in cancer patients by very low doses of a T-cell engaging antibody. *Science.* 231: 974-7 (2008).
Caldas et al., Humanization of the anti-CD18 antibody 6.7: an unexpected effect of a framework residue in binding to antigen, *Mol. Immunol.* 39:941-52 (2003).
Cancer Network, (Nov. 1, 2007, pp. 1-2).
Chien et al., Significant structural and functional change of an antigen-binding site by a distant amino acid substitution: proposal of a structural mechanism, *Proc. Natl. Acad. Sci. USA.* 86:5532-6 (1989).
Cole-Sinclair et al., Genetic changes: relevance for diagnosis and detection of minimal residual disease in acute lymphoblastic leukaemia, *Baillieres Clin. Haematol.* 7:183-233 (244).
International Search Report received in the corresponding International Patent Application No. PCT/EP2009/007970, dated Mar. 10, 2010.
Office Action received in the related U.S. Appl. No. 13/127,538, dated Sep. 25, 2012.
Csoka, et al. "Activation of T cell cytotoxicity against autologous common acute lymphoblastic leukemia (cALL) blasts by CD3xCD19 bispecific antibody," *Leukemia.* 10:1765-1772 (1996).
Evaluate Press Release (Jun. 12, 2008, pp. 1-2).
Giusti et al., Somatic diversification of S107 from an antiphosphocholine to an anti-DNA autoantibody is due to a single base change in its heavy chain variable region, *Proc. Natl. Acad. Sci. USA.* 84:2926-30 (1987).
Gokbuget et al., Treatment with monoclonal antibodies in acute lymphoblastic leukemia: current knowledge and future prospects, *Ann. Hematol.* 83:201-5 (2004).
Goulet et al., Conjugation of blocked ricin to an anti-CD19 monoclonal antibody increases antibody-induced cell calcium mobilization and CD19 internalization. *Blood.* 90: 2364-75 (1997).
Gussow et al., Humanization of monoclonal antibodies, *Methods Enzymol.* 203:99-121 (1991).
Haagen et al., Killing of autologous B-lineage malignancy using CD3 x CD19 bispecific monoclonal antibody in end stage leukemia and lymphoma, *Blood.* 84:556-63 (1994).
Jeha, New Therapeutic Strategies in Acute Lymphoblastic Leukemia, *Seminars in Hematology.* 46:76-88 (2009).

(Continued)

*Primary Examiner* — Brad Duffy
(74) *Attorney, Agent, or Firm* — Marshall, Gerstein & Borun LLP

(57) ABSTRACT

The present invention relates to a method for the treatment, amelioration or elimination of acute lymphoblastic leukemia (ALL), the method comprising the administration of a pharmaceutical composition comprising a CD19×CD3 bispecific single chain antibody construct to an adult patient in the need thereof.

21 Claims, 8 Drawing Sheets

Figure 1:
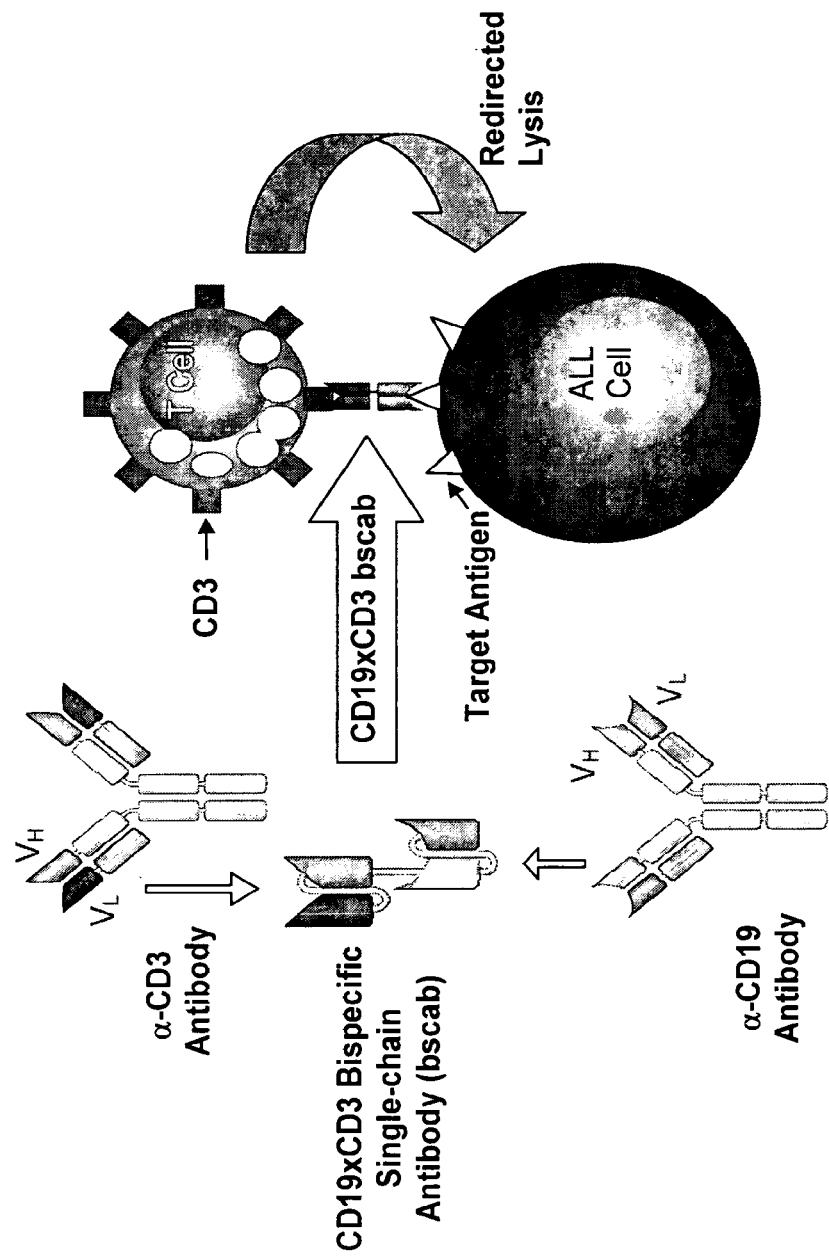

Specification includes a Sequence Listing.

(56) References Cited

OTHER PUBLICATIONS

Kipriyanov et al., Bispecific CD3 x CD19 diabody for T cell-mediated lysis of malignant human B cells, *Int. J. Cancer.* 77:763-72 (1998).

Kufer et al., Construction and biological activity of a recombinant bispecific single-chain antibody designed for therapy of minimal residual colorectal cancer, *Cancer Immunol. Imunother.* 45:193-7 (1997).

Loffler et al., A recombinant bispecific single-chain antibody, CD19 x CD3, induces rapid and high lymphoma-directed cytotoxicity by unstimulated T lymphocytes, *Blood.* 95:2098-103 (2000).

Mariuzza et al., The structural basis of antigen-antibody recognition, *Annu. Rev. Bophys. Chem.* 16:139-59 (1987).

Molhoj et al., CD19-/CD3-bispecific antibody of the BiTE class is far superior to tandem diabody with respec to redirected tumor cell lysis, *Mol. Immunol.* 44:1945-53 (2007).

Office Action from European Application No. 09760483.9 dated Sep. 12, 2013.

Office Action issued in Chinese Application No. 200980144399.8 dated Jan. 28, 2013.

Open-Label, Multicenter Phase II Study to Investigate the Efficacy, Safety, and Tolerability of the Bispecific T-Cell Engager (BiTE®) MT103 in Patients with Minimal Residual Disease of B-Precursor Acute Lymphoblastic Leukemia. Micromet AG, ClinicalTrails.gov, NCT00560794, dated Aug. 11, 2008.

Peham et al., Low frequency of clonotypic Ig and T-cell receptor gene rearrangements in t(4;11) infant acute lymphoblastic leukaemia and its implication for the detection of minimal residual disease, *Br. J. Haematol.* 117:315-21 (2002).

PR Newswire, Micromet Receives Regulatory Approval to Conduct a Phase 2 Clinical Trial Investigating MT103 (MEDI-538) in Patients with Acute Lympholastic Leukemia, pp. 1-4, Oct. 18, 2007.

Rudikoff et al., Single amino acid substitution altering antigen-binding specificity, *Proc. Natl. Acad. Sci. USA.* 79:1979-83 (1982).

Search Report from Chinese Application No. 200980144399.8 dated Jan. 17, 2013.

Spinelli et al., Clearance of minimal residual disease after allogeneic stem cell transplantation and the prediction of the clinical outcome of adult patients with high-risk acute lymphoblastic leukemia, *Haematologica.* 92:612-8 (2007).

Sramkova et al., Detectable minimal residual disease before allogeneic hematopoietic stem cell transplantation predicts extremely poor prognosis in children with acute lymphoblastic leukemia, *Pediatr. Blood Cancer.* 48:93-100 (2007).

Topp, et al., "Targeted Therapy with the T-Cell-Engaging Antibody Blinatumomab of Chemotherapy-Refractory Minimal Residual Disease in B-Lineage Acute Lymphoblastic Leikemia Patients Results in High Response Rate and Prolonged Leukemia-Free Survival," *Journal of Clinical Oncology.* 29:2493-2498 (2011).

Topp et al., Treatment of Anti-CD19 BiTE Antibody Blinatumomab (MT103/MEDI-538) is able to Eliminate Minimal Residual Disease (MRD) in Patients with B-Precursor Acute Lymphoblastic Leukemia (ALL): First Results of an Ongoing Phase II Study, *American-Society-of-Hematology*, 112:672-3 (2008).—Abstract only.

Topp et al., Treatment with Anti-CD19 BiTE Antibody Blinatumomab (MT103 / MEDI-538) is Able to Eliminate Minimal Residual Disease (MRD) in Patients with B-Precursor Acute Lymphoblastic Leukemia (ALL): First Results of an Ongoing Phase II Study, *Blood.* 112:1926 (Abstract Only) (2008).

Winkler et al., Changing the antigen binding specificity by single point mutations of an anti-p24 (HIV-1) antibody, *J. Immunol.* 165:4505-14 (2000).

* cited by examiner

Figure 5

| Patient number | Gender age | Diagnosis | MRD |
|---|---|---|---|
| 111001 | Female 31 years | c-ALL | Ig-rearrangement |
| 108001 | Female 57 years | Pre-B-ALL | Ig-rearrangement |
| 109002 | Male 62 years | c-ALL | TCR-rearrangement |
| 110002 | Male 65 years | c-ALL | bcr/abl |

Figure 6

| Patient no. | Screening | MRD status after first cycle | Follow up |
|---|---|---|---|
| 111001 | $8 \times 10^{-4}$ | Negative | MRD negative from 23.06.2008 to 27.10.2008 Successful allogeneic stem cell transplantation No relapse to date |
| 108001 | $1 \times 10^{-3}$ | Negative | Ongoing negative MRD status since 07/28/2008 |
| 109002 | $1 \times 10^{-1}$ | Negative | Testicular relapse followed by hematological relapse after 19 weeks of MRD-negativity |
| 110002 | bcr/abl $1.73 \times 10^{-4}$ | $5.54 \times 10^{-4}$ | Ongoing stable MRD status |

Figure 7

| | Number of patients | MRD-negativity achieved |
|---|---|---|
| Individual rearrangements (Immunoglobulin or TCR) | 11 | 9 |
| t(4;11) translocation | 2 | 1 |
| Bcr/abl positive | 4 | 3 |
| total | 17 | 13 |
| MRD response rate among 16 evaluable patients | | 81% |

SEQUENCE LISTING

```
<160> NUMBER OF SEQ ID NOS: 22

<210> SEQ ID NO 1
<211> LENGTH: 498
<212> TYPE: PRT
<213> ORGANISM: Artificial Sequence
<220> FEATURE:
<223> OTHER INFORMATION: ="Description of artificial sequence: CD19xCD3
      bispecific single chain antibody"

<400> SEQUENCE: 1

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80
```

-continued

```
Pro Val Glu Lys Val Asp Ala Ala Thr Tyr His Cys Gln Gln Ser Thr
                 85                  90                  95
Glu Asp Pro Trp Thr Phe Gly Gly Gly Thr Lys Leu Glu Ile Lys Gly
            100                 105                 110
Gly Gly Gly Ser Gly Gly Gly Gly Ser Gly Gly Gly Gly Ser Gln Val
            115                 120                 125
Gln Leu Gln Gln Ser Gly Ala Glu Leu Val Arg Pro Gly Ser Ser Val
        130                 135                 140
Lys Ile Ser Cys Lys Ala Ser Gly Tyr Ala Phe Ser Ser Tyr Trp Met
145                 150                 155                 160
Asn Trp Val Lys Gln Arg Pro Gly Gln Gly Leu Glu Trp Ile Gly Gln
                165                 170                 175
Ile Trp Pro Gly Asp Gly Asp Thr Asn Tyr Asn Gly Lys Phe Lys Gly
            180                 185                 190
Lys Ala Thr Leu Thr Ala Asp Glu Ser Ser Ser Thr Ala Tyr Met Gln
        195                 200                 205
Leu Ser Ser Leu Ala Ser Glu Asp Ser Ala Val Tyr Phe Cys Ala Arg
    210                 215                 220
Arg Glu Thr Thr Thr Val Gly Arg Tyr Tyr Ala Met Asp Tyr Trp
225                 230                 235                 240
Gly Gln Gly Thr Thr Val Thr Val Ser Ser Gly Gly Gly Gly Ser Asp
                245                 250                 255
Ile Lys Leu Gln Gln Ser Gly Ala Glu Leu Ala Arg Pro Gly Ala Ser
            260                 265                 270
Val Lys Met Ser Cys Lys Thr Ser Gly Tyr Thr Phe Thr Arg Tyr Thr
        275                 280                 285
Met His Trp Val Lys Gln Arg Pro Gly Gln Gly Leu Glu Trp Ile Gly
    290                 295                 300
Tyr Ile Asn Pro Ser Arg Gly Tyr Thr Asn Tyr Asn Gln Lys Phe Lys
305                 310                 315                 320
Asp Lys Ala Thr Leu Thr Thr Asp Lys Ser Ser Ser Thr Ala Tyr Met
                325                 330                 335
Gln Leu Ser Ser Leu Thr Ser Glu Asp Ser Ala Val Tyr Tyr Cys Ala
            340                 345                 350
Arg Tyr Tyr Asp Asp His Tyr Cys Leu Asp Tyr Trp Gly Gln Gly Thr
        355                 360                 365
Thr Leu Thr Val Ser Ser Val Glu Gly Gly Ser Gly Gly Ser Gly Gly
    370                 375                 380
Ser Gly Gly Ser Gly Gly Val Asp Asp Ile Gln Leu Thr Gln Ser Pro
385                 390                 395                 400
Ala Ile Met Ser Ala Ser Pro Gly Glu Lys Val Thr Met Thr Cys Arg
                405                 410                 415
Ala Ser Ser Ser Val Ser Tyr Met Asn Trp Tyr Gln Gln Lys Ser Gly
            420                 425                 430
Thr Ser Pro Lys Arg Trp Ile Tyr Asp Thr Ser Lys Val Ala Ser Gly
        435                 440                 445
Val Pro Tyr Arg Phe Ser Gly Ser Gly Ser Gly Thr Ser Tyr Ser Leu
    450                 455                 460
Thr Ile Ser Ser Met Glu Ala Glu Asp Ala Ala Thr Tyr Tyr Cys Gln
465                 470                 475                 480
Gln Trp Ser Ser Asn Pro Leu Thr Phe Gly Ala Gly Thr Lys Leu Glu
                485                 490                 495
Leu Lys
```

<210> SEQ ID NO 2
<211> LENGTH: 1494
<212> TYPE: DNA
<213> ORGANISM: Artificial Sequence
<220> FEATURE:
<223> OTHER INFORMATION: ="Description of artificial sequence: CD19xCD3 bispecific single chain antibody"

<400> SEQUENCE: 2

```
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaaggtggtg gtggttctgg cggcggcggc      360
tccggtggtg gtggttctca ggtgcagctg cagcagtctg ggctgagct ggtgaggcct      420
gggtcctcag tgaagatttc ctgcaaggct tctggctatg cattcagtag ctactggatg     480
aactgggtga agcagaggcc tggacagggt cttgagtgga ttggacagat ttggcctgga     540
gatggtgata ctaactacaa tggaaagttc aagggtaaag ccactctgac tgcagacgaa     600
tcctccagca cagcctacat gcaactcagc agcctagcat ctgaggactc tgcggtctat     660
ttctgtgcaa gacgggagac tacgacggta ggccgttatt actatgctat ggactactgg     720
ggccaaggga ccacggtcac cgtctcctcc ggaggtggtg gatccgatat caaactgcag     780
cagtcagggg ctgaactggc aagacctggg gcctcagtga agatgtcctg caagacttct     840
ggctacacct ttactaggta cacgatgcac tgggtaaaac agaggcctgg acagggtctg     900
gaatggattg gatacattaa tcctagccgt ggttatacta attacaatca gaagttcaag     960
gacaaggcca cattgactac agacaaatcc tccagcacag cctacatgca actgagcagc    1020
ctgacatctg aggactctgc agtctattac tgtgcaagat attatgatga tcattactgc    1080
cttgactact ggggccaagg caccactctc acagtctcct cagtcgaagg tggaagtgga    1140
ggttctggtg aagtggagg ttcaggtgga gtcgacgaca ttcagctgac ccagtctcca    1200
gcaatcatgt ctgcatctcc aggggagaag gtcaccatga cctgcagagc cagttcaagt    1260
gtaagttaca tgaactggta ccagcagaag tcaggcacct cccccaaaag atggatttat    1320
gacacatcca aagtggcttc tggagtccct tatcgcttca gtggcagtgg gtctgggacc    1380
tcatactctc tcacaatcag cagcatggag gctgaagatg ctgccactta ttactgccaa    1440
cagtggagta gtaacccgct cacgttcggt gctgggacca agctggagct gaaa           1494
```

<210> SEQ ID NO 3
<211> LENGTH: 124
<212> TYPE: PRT
<213> ORGANISM: Artificial Sequence
<220> FEATURE:
<223> OTHER INFORMATION: ="Description of artificial sequence: VH anti CD19"

<400> SEQUENCE: 3

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30
```

```
Trp Met Asn Trp Val Lys Gln Arg Pro Gly Gln Gly Leu Glu Trp Ile
         35                  40                  45

Gly Gln Ile Trp Pro Gly Asp Gly Asp Thr Asn Tyr Asn Gly Lys Phe
 50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser
        115                 120
```

<210> SEQ ID NO 4
<211> LENGTH: 372
<212> TYPE: DNA
<213> ORGANISM: Artificial Sequence
<220> FEATURE:
<223> OTHER INFORMATION: ="Description of artificial sequence: VH anti
      CD19"

<400> SEQUENCE: 4

```
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg gagatggtga ctactaactac    180
aatgaaagt tcaagggtaa agccactctg actgcagacg aatcctccag cacagcctac      240
atgcaactca gcagcctagc atctgaggac tctgcggtct atttctgtgc aagacgggag     300
actacgacgg taggccgtta ttactatgct atggactact ggggccaagg gaccacggtc     360
accgtctcct cc                                                         372
```

<210> SEQ ID NO 5
<211> LENGTH: 111
<212> TYPE: PRT
<213> ORGANISM: Artificial Sequence
<220> FEATURE:
<223> OTHER INFORMATION: ="Description of artificial sequence: VL anti
      CD19"

<400> SEQUENCE: 5

```
Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                 20                  25                  30

Gly Asp Ser Tyr Leu Asn Trp Tyr Gln Gln Ile Pro Gly Gln Pro Pro
             35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
                100                 105                 110
```

<210> SEQ ID NO 6
<211> LENGTH: 333
<212> TYPE: DNA

```
<213> ORGANISM: Artificial Sequence
<220> FEATURE:
<223> OTHER INFORMATION: ="Description of artificial sequence: VL anti
      CD19"

<400> SEQUENCE: 6
gatatccagc tgacccagtc tccagcttct ttggctgtgt ctctagggca gagggccacc     60
atctcctgca aggccagcca aagtgttgat tatgatggtg atagttattt gaactggtac    120
caacagattc caggacagcc acccaaactc ctcatctatg atgcatccaa tctagtttct    180
gggatcccac ccaggtttag tggcagtggg tctgggacag acttcaccct caacatccat    240
cctgtggaga aggtggatgc tgcaacctat cactgtcagc aaagtactga ggatccgtgg    300
acgttcggtg agggaccaa gctcgagatc aaa                                  333

<210> SEQ ID NO 7
<211> LENGTH: 119
<212> TYPE: PRT
<213> ORGANISM: Artificial Sequence
<220> FEATURE:
<223> OTHER INFORMATION: ="Description of artificial sequence: VH anti
      CD3"

<400> SEQUENCE: 7

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 8
<211> LENGTH: 357
<212> TYPE: DNA
<213> ORGANISM: Artificial Sequence
<220> FEATURE:
<223> OTHER INFORMATION: ="Description of artificial sequence: VH anti
      CD3"

<400> SEQUENCE: 8
gatatcaaac tgcagcagtc aggggctgaa ctggcaagac ctggggcctc agtgaagatg     60
tcctgcaaga cttctggcta cacctttact aggtacacga tgcactgggt aaaacagagg    120
cctggacagg gtctggaatg gattggatac attaatccta gccgtggtta tactaattac    180
aatcagaagt tcaaggacaa ggccacattg actacagaca atcctccag cacagcctac     240 atgcaactga gcagcctgac atctgaggac tctgcagtct attactgtgc aagatattat    300
gatgatcatt actgccttga ctactggggc caaggcacca ctctcacagt ctcctca      357

<210> SEQ ID NO 9
```

<211> LENGTH: 106
<212> TYPE: PRT
<213> ORGANISM: Artificial Sequence
<220> FEATURE:
<223> OTHER INFORMATION: ="Description of artificial sequence: VL anti CD3"

<400> SEQUENCE: 9

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105
```

<210> SEQ ID NO 10
<211> LENGTH: 318
<212> TYPE: DNA
<213> ORGANISM: Artificial Sequence
<220> FEATURE:
<223> OTHER INFORMATION: ="Description of artificial sequence: VL anti CD3"

<400> SEQUENCE: 10

```
gacattcagc tgacccagtc tccagcaatc atgtctgcat ctccagggga gaaggtcacc      60
atgacctgca gccagttc aagtgtaagt tacatgaact ggtaccagca gaagtcaggc       120
acctccccca aaagatggat ttatgacaca tccaaagtgg cttctggagt cccttatcgc     180
ttcagtggca gtgggtctgg gacctcatac tctctcacaa tcagcagcat ggaggctgaa     240
gatgctgcca cttattactg ccaacagtgg agtagtaacc cgctcacgtt cggtgctggg     300
accaagctgg agctgaaa                                                   318
```

<210> SEQ ID NO 11
<211> LENGTH: 15
<212> TYPE: PRT
<213> ORGANISM: artificial sequence
<220> FEATURE:
<223> OTHER INFORMATION: ="Description of artificial sequence: anti-CD19 L1"

<400> SEQUENCE: 11

```
Lys Ala Ser Gln Ser Val Asp Tyr Asp Gly Asp Ser Tyr Leu Asn
1               5                   10                  15
```

<210> SEQ ID NO 12
<211> LENGTH: 7
<212> TYPE: PRT
<213> ORGANISM: artificial sequence
<220> FEATURE:
<223> OTHER INFORMATION: ="Description of artificial sequence: anti-CD19 L2"

```
<400> SEQUENCE: 12

Asp Ala Ser Asn Leu Val Ser
1               5

<210> SEQ ID NO 13
<211> LENGTH: 9
<212> TYPE: PRT
<213> ORGANISM: artificial sequence
<220> FEATURE:
<223> OTHER INFORMATION: ="Description of artificial sequence: anti-CD19
      L3"

<400> SEQUENCE: 13

Gln Gln Ser Thr Glu Asp Pro Trp Thr
1               5

<210> SEQ ID NO 14
<211> LENGTH: 5
<212> TYPE: PRT
<213> ORGANISM: artificial sequence
<220> FEATURE:
<223> OTHER INFORMATION: ="Description of artificial sequence:  anti-
      CD19 H1"

<400> SEQUENCE: 14

Ser Tyr Trp Met Asn
1               5

<210> SEQ ID NO 15
<211> LENGTH: 17
<212> TYPE: PRT
<213> ORGANISM: artificial sequence
<220> FEATURE:
<223> OTHER INFORMATION: ="Description of artificial sequence:  anti-
      CD19 H2"

<400> SEQUENCE: 15

Gln Ile Trp Pro Gly Asp Gly Asp Thr Asn Tyr Asn Gly Lys Phe Lys
1               5                   10                  15

Gly

<210> SEQ ID NO 16
<211> LENGTH: 15
<212> TYPE: PRT
<213> ORGANISM: artificial sequence
<220> FEATURE:
<223> OTHER INFORMATION: ="Description of artificial sequence: anti-CD19
      H3"

<400> SEQUENCE: 16

Arg Glu Thr Thr Thr Val Gly Arg Tyr Tyr Tyr Ala Met Asp Tyr
1               5                   10                  15

<210> SEQ ID NO 17
<211> LENGTH: 5
<212> TYPE: PRT
<213> ORGANISM: artificial sequence
<220> FEATURE:
<223> OTHER INFORMATION: ="Description of artificial sequence: anti-CD3
      H1"

<400> SEQUENCE: 17

Arg Tyr Thr Met His
1               5
```

-continued

```
<210> SEQ ID NO 18
<211> LENGTH: 17
<212> TYPE: PRT
<213> ORGANISM: artificial sequence
<220> FEATURE:
<223> OTHER INFORMATION: ="Description of artificial sequence: anti-CD3
      H2"

<400> SEQUENCE: 18

Tyr Ile Asn Pro Ser Arg Gly Tyr Thr Asn Tyr Asn Gln Lys Phe Lys
1               5                   10                  15
Asp

<210> SEQ ID NO 19
<211> LENGTH: 10
<212> TYPE: PRT
<213> ORGANISM: artificial sequence
<220> FEATURE:
<223> OTHER INFORMATION: ="Description of artificial sequence: anti-CD3
      H3"

<400> SEQUENCE: 19

Tyr Tyr Asp Asp His Tyr Cys Leu Asp Tyr
1               5                   10

<210> SEQ ID NO 20
<211> LENGTH: 10
<212> TYPE: PRT
<213> ORGANISM: artificial sequence
<220> FEATURE:
<223> OTHER INFORMATION: ="Description of artificial sequence: anti-CD3
      L1"

<400> SEQUENCE: 20

Arg Ala Ser Ser Ser Val Ser Tyr Met Asn
1               5                   10

<210> SEQ ID NO 21
<211> LENGTH: 7
<212> TYPE: PRT
<213> ORGANISM: artificial sequence
<220> FEATURE:
<223> OTHER INFORMATION: ="Description of artificial sequence: anti-CD3
      L2"

<400> SEQUENCE: 21

Asp Thr Ser Lys Val Ala Ser
1               5

<210> SEQ ID NO 22
<211> LENGTH: 9
<212> TYPE: PRT
<213> ORGANISM: artificial sequence
<220> FEATURE:
<223> OTHER INFORMATION: ="Description of artificial sequence: anti-CD3
      L3"

<400> SEQUENCE: 22

Gln Gln Trp Ser Ser Asn Pro Leu Thr
1               5
```

TREATMENT OF ACUTE LYMPHOBLASTIC LEUKEMIA

The present invention relates to a method for the treatment, amelioration or elimination of acute lymphoblastic leukemia (ALL), the method comprising the administration of a pharmaceutical composition comprising a CD19×CD3 bispecific single chain antibody construct to an adult patient in the need thereof.

Leukemias are clonal neoplastic proliferations of immature hematopoietic cells that are characterized by aberrant or arrested differentiation. Leukemia cells accumulate in the bone marrow, ultimately replacing most of normal hematopoietic cells. This results in bone marrow failure and its consequences of anemia, hemorrhage and infection. Leukemia cells circulate into the blood and other tissues throughout the body (DeVita, Hellmann, Rosenberg. Cancer: principles and practice of oncology. Eight edition. Library of Congress Cataloging-in-Publication Data, ISBN 0-781-72387-6). The acute leukemias, which can be broadly grouped as either lymphoblastic or myeloblastic can be identified phenotypically and genetically and are characterized by a rapid clinical course requiring immediate treatment. Acute leukemia's are derived from early hematopoietic progenitor cells. In contrast chronic leukemia's have the phenotype and biologic character of more mature cells (DeVita et al., loc. cit.). Acute lymphoblastic leukemia (ALL) is distinguished from the lymphomas because the latter resemble more mature lymphoid cells and typically inhabit the lymph nodes, spleen or other extramedullary sites before spreading to the bone marrow. Certain lymphomas such as lymphoblastic lymphomas or Burkitt's lymphomas retain features of both the leukemia's and lymphomas but are derived from immature progenitor cells and require therapy similar to that used for acute lymphoblastic leukemia ALL). Other lymphomas however may spread widely into the blood and bone marrow, and in such a phase can be described as leukemic lymphomas but are not true leukemias (De Vita et al., loc. cit.).

Acute lymphoblastic leukemia is a relatively rare malignancy. The total incidence of acute lymphoblastic leukemia (ALL) is 1.1/100,000 per year. The incidence has its peak during childhood, decreasing continuously with increasing age. From the age of 35 years on the incidence rises again and a second peak is observed starting from the age of 80 years (2.3/100,000 per year) (Hoelzer and Gökbuget; Der Onkologe 12 (2006); 983-1002). Although the etiology of acute lymphoblastic leukemia (ALL) is unclear, it is one of the most carefully studied and best characterized neoplasms. The acute lymphoblastic leukemia (ALL) subgroups are defined mainly by immunophenotyping, cytogentics and molecular genetics. B-lineage acute lymphoblastic leukemia (ALL) with 74% of cases comprises the majority of ALL's. Seventy percent of all ALL's are B-precursor ALL's and 4% are mature B-cell ALL's. T-lineage ALL's covers 26% of all ALL's (Hoelzer and Gökbuget; Der Onkologe 12 (2006); 983-1002).

In the early 1980s, adult acute lymphoblastic leukemia (ALL) was a rarely curable disease with an overall survival of less than 10%. After use of adapted regimens administered by pediatric groups the outcome improved to 30-40%. A period of stagnation followed with improvement only in distinct subgroups. However, in the last five years, progress has been made in molecular diagnostics of acute lymphoblastic leukemia (ALL). Stem cell transplantation (SCT) has improved the outcome of acute lymphoblastic leukemia (ALL) and has made treatment more feasible. Though various new targeted drugs are under evaluation, effective targeted therapies for acute lymphoblastic leukemia (ALL) are not yet available. Rapid diagnosis and classification of acute lymphoblastic leukemia (ALL) is increasingly important to identify prognostic and molecular genetic subsets that will be the focus of targeted treatment (Hoelzer and Gökbuget; Hematology (2006); 133-141). The Philadelphia chromosome (Ph), the result of a reciprocal translocation fusing the abl proto-oncogene from chromosome 9 with the breakpoint cluster region sequences on chromosome 22, was the first neoplasm-specific translocation to be identified. Translocation (9;22) is the most frequent genetic aberration in adult acute lymphoblastic leukemia (ALL). It is found in 20-30% of patients. The incidence increases with age, approaching 50% in patients older than 50 years. In past clinical studies, older patients were underrepresented due to the perceived futility of treatment, but this pattern is changing with the availability of promising novel treatment options. Notably, it is found almost exclusively in CD10+ precursor B-cell acute lymphoblastic leukemia (c-ALL and pre-B ALL); rare reports of its presence in T-lineage ALL may represent chronic myeloid leukemia (CML) in lymphoid blast crisis rather than bona fide Ph+ ALL. Clinically, patients present with a variable white blood cell (WBC) count, surface expression of CD19, CD10 and CD34 antigens, and frequent co-expression of myeloid markers, e.g., CD13 and CD33, have an increased risk of developing meningeal leukemia. The prognosis of adult patients with Ph+ ALL treated only with chemotherapy is poor, with a less than 10% probability of long-term survival. Because of the dismal outcome with chemotherapy, allogeneic hematopoietic stem cell transplantation (HSCT) is currently considered to be the treatment of choice in adult Ph+ ALL. 12% to 65% long-term survival rates have been reported for patients undergoing SCT in first complete remission (CR), indicating that this procedure is potentially curative. However, approximately 30% of these patients experience relapses (Ottmann and Wassmann; Hematology (2005), 118-122). The presence of leukemia cells below the cytological detection limit (5% leukemic cells) is defined as minimal residual disease (MRD). If no MRD is detectable ($<10^4$, i.e. <1 leukemia cell per $10^4$ bone marrow cells) a complete molecular remission is reached. In the last years, a series of retrospective studies has shown that MRD in adult acute lymphoblastic leukemia is an independent prognostic factor as already demonstrated for childhood leukemia. Diagnostic tools for MRD are polymerase chain reaction (PCR) and/or flow cytometry. PCR analysis can detect fusion transcripts such as bcr/abl and individual clonal rearrangements of immunoglobulins (IgH) and/or T-cell receptor genes (TCR). About 25% of patients with minimal residual disease (MRD) defined by rearrangement comprise a high-risk group with a 94% relapse rate within 3 years. In general, the decrease in MRD occurs more slowly in adults than it does in children. Decision making about treatment intensification by allogeneic peripheral blood stem cell transplantation (PBSCT) is therefore too early after induction treatment. However, after start of consolidation, minimal residual disease (MRD) at any time point is associated with a high risk of relapse (Brüggemann et al., Blood 107 (2006), 1116-1123; Raff et al., Blood 109 (2007), 910-915).

Treatment of adult patients with acute lymphoblastic leukemia (ALL) is becoming increasingly complex as diverse treatment protocols are introduced for different subtypes of the disease, reflecting the intention to optimally tailor therapy to specific risk-adapted disease entities. Recent improvements have been achieved by introducing new therapeutic principles, such as the early addition of the tyrosine kinase inhibitor imatinib in Ph-positive (Ph+) ALL (Lee et al., Blood 102 (2003), 3068-3070) or the use of the anti-CD20 antibody rituximab in CD20+ cases of B-lineage ALL (see e.g. Griffin et al., Pediatr Blood Cancer 2008). Diagnostic improvements were achieved by assessing the level of minimal residual disease (MRD) either by molecular genetic methods or by flow cytometry, which has been shown to be predictive for outcome in a number of studies in children (see e.g. Cave et al., N. Engl. J. Med. 339 (1998), 591-598) and adults (see e.g. Brüggemann et al., Blood 107 (2006), 1116-1123). Survival rates with modern treatment protocols for adult acute lymphoblastic leukemia (ALL) patients have reached a plateau where the potential benefit of more aggressive chemotherapeutic regimens is often offset by an excess mortality due to complications, thus making efforts to individualize treatment even more important. Whereas standard-risk patients without conventional risk factors, who have a greater than 50% chance of long-term survival with chemotherapy alone (Hoelzer et al., Hematology Am. Soc. Hematol. Educ. Program 1 (2002), 162-192) are potentially put at unnecessary risk by intensified and prolonged therapy, outcome in patients with relapsed acute lymphoblastic leukemia (ALL) is extremely poor, even if a second remission is achieved. In a recent study, minimal residual disease (MRD) monitoring during the first year of intensive chemotherapy led to an MRD-based risk stratification (Brüggemann et al. (2006), loc. cit.). This classification allowed the identification of an MRD low-risk group consisting of about 10% of patients with a minimal chance of relapse at 3 years, an MRD high-risk group of about 25% of patients with an almost 100% risk of relapse, and an MRD intermediate-risk group. In the latter group, about 30% of patients will eventually relapse despite becoming MRD negative or reaching MRD levels below $10^{-4}$ at the end of the first year of therapy.

These data show that acute lymphoblastic leukemia (ALL) remains for most patients a fulminate and incurable disease. In light of this, there is an urgent need for improved ALL therapies.

The present invention provides for a method for the treatment, amelioration or elimination of acute lymphoblastic leukemia (ALL), the method comprising the administration of a pharmaceutical composition comprising a CD19×CD3 bispecific single chain antibody construct to an adult patient in the need thereof. In a preferred embodiment of the pharmaceutical methods and means of the invention, said acute lymphoblastic leukemia (ALL) is B-lineage acute lymphoblastic leukemia (ALL), preferably B-precursor acute lymphoblastic leukemia. B-lineage acute lymphoblastic leukemia (ALL) comprises the majority of ALL's with 74% of cases. Seventy percent of all ALL's are B-precursor ALL's and 4% are mature B-cell ALL's. Since the CD19×CD3 bispecific single chain antibody described herein is directed against the B cell-associated marker CD19, said antibody is particularly suitable as a therapeutic agent for B-lineage acute lymphoblastic leukemia, preferably for B-precursor ALL's which can be further subdivided into pro-B ALL, pre-B ALL and common ALL (cALL).

The administration of the CD19×CD3 bispecific single chain antibody (also termed blinatumomab or MT103) described in more detail below provides for the first time a therapeutic approach which allows the treatment of minimal residual disease in patients with acute lymphoblastic leukemia (ALL). As shown in the following examples and illustrated by FIG. 1, the CD19×CD3 bispecific single chain antibody (the nucleic acid sequence and amino acid sequence of which is depicted in SEQ ID NOs. 2 and 1, respectively) has been designed to link T cells with CD19-expressing target cells resulting in a non-restricted cytotoxic T-cell response and T-cell activation. Recently, a phase I study has demonstrated significant clinical activity of the CD19×CD3 bispecific single chain antibody in relapsed B-cell non-Hodgkin's lymphoma (NHL) (Bargou et al., Science 321 (2008):974-7). Based on these results, a phase II study was designed in collaboration with the German Multicenter Study Group on Adult Acute Lymphoblastic Leukemia (GMALL) to investigate efficacy, safety, and tolerability of the CD19×CD3 bispecific single chain antibody in acute lymphoblastic leukemia (ALL) patients who achieved a complete hematological remission, but still had minimal residual disease (MRD). MRD is an independent prognostic factor that reflects primary drug resistance and is associated with a high relapse risk after start of consolidation. MRD was measured with standardized methods either by quantitative detection of individual rearrangements of immunoglobulin or T-cell receptor (TCR) rearrangements, t(4;11) translocations or by bcr/abl fusion transcripts (see e.g. Van der Velden et al., Leukemia 18 (2004), 1971-80). The study population includes adult patients with acute B-precursor acute lymphoblastic leukemia (ALL) who show a bcr/abl signal or t(4;11) signal above detection limit and/or at least one marker by rearrangement with a sensitivity of $\geq 10^{-4}$. Primary endpoint of the ongoing phase II study is the conversion rate to minimal residual disease (MRD) negative status as defined by a bcr/abl or a t(4;11) signal below detection limit and/or by detection of individual rearrangements of immunoglobulin or T-cell receptor (TCR) genes below $10^{-4}$. One treatment cycle of the CD19×CD3 bispecific single chain antibody is a 4-week continuous intravenous infusion, which can be followed by allogeneic hematopoietic stem cell transplantation after the first cycle, or by repeated cycles after a 2-week treatment-free interval. The dosage of CD19×CD3 bispecific single chain antibody is 15 microgram/m²/24 hr, whereby an intra-patient dose escalation up to 30 microgram/m²/24 hr is allowed. Minimal residual disease (MRD) status is controlled after each treatment cycle. Patients who achieve MRD negativity might receive additional treatment cycles.

To date, seventeen adult ALL patients have been treated, or are still on treatment with the CD19×CD3 bispecific single chain antibody. 14 patients received the dose level of 15 microgram/m²/24 hr of CD19×CD3 bispecific single chain antibody, whereas in three patients the dose has been escalated from 15 to 30 microgram/m²/24 hr after the first or further treatment cycles. All of these ALL patients had minimal residual disease (MRD): Eleven of them had MRD by immunoglobulin or TCR rearrangements, two patients had t(4;11) translocations and four patient had bcr/abl fusion transcripts.

As a result, MRD response was evaluable in 16 of 17 patients. 13 of 16 patients became MRD negative, which corresponds to an extraordinary complete molecular response rate of 81%. More specifically, in nine out of eleven patients with immunoglobulin or TCR rearrangements, in one out of two patients with t(4;11) translocations and in three out of four patients with bcr/abl transcripts, MRD-negativity could be achieved. The longest duration of MRD-negativity observed so far in a patient having not received a transplantation after the antibody treatment is 41 weeks. Another patient treated with the CD19×CD3 bispecific single chain antibody with MRD-negativity from 23

Jun. 2008 to 27 Oct. 2008 and having received a successful allogeneic stem cell transplantation thereafter is relapse-free to date.

Remarkably, the bcr/abl patients who could successfully be treated with the CD19×CD3 bispecific single chain antibody were refractory or intolerant to tyrosine kinase inhibitors imatinib and/or dasatinib in previous ALL treatment regimen. For example, one of the bcr/abl responders to treatment with CD19×CD3 bispecific single chain antibody had a T315I mutation which was refractory to therapy by tyrosine kinase inhibitors. Thus, the administration of the CD19×CD3 bispecific single chain antibody now provides for the first time for a therapy for imatinib- and/or dasatinib-refractory ALL patients with bcr/abl transcripts. Only three out of a total of 17 patients did not become MRD negative. However, in two of them stable disease could be achieved. Only one patient had a testicular relapse followed by a hematological relapse, after 19 weeks of MRD-negativity. One patient was not evaluable due to a serious adverse event (SAE) on study day 2.

In summary, an absolutely exceptional complete molecular response rate of 81% could be achieved in adult patients with B-precursor ALL upon treatment with the CD19×CD3 bispecific single chain antibody. Activity of the mentioned antibody could be observed in all ALL patient subsets treated, including tyrosine kinase inhibitors-refractory (T315I) bcr/abl patients and patients with t(4;11) translocations. These ALL patient subsets are generally considered incurable by conventional ALL standard therapy, except for the option of allogeneic HSCT. In addition, treatment with CD19×CD3 bispecific single chain antibody shows a favorable toxicity profile, in contrast to conventional ALL therapies, such as chemotherapy. In light of this, the administration of the CD19×CD3 bispecific single chain antibody described herein provides a new and advantageous treatment option for adult acute lymphoblastic leukemia (ALL), in particular for cases in which the ALL is refractory to conventional ALL therapy, such as chemotherapy and/or allogeneic HSCT. In addition, the administration of the CD19×CD3 bispecific single chain antibody now provides for the first time for a therapy for MRD-positive ALL.

The method of the present invention provides for the following major advantages:

1. Less adverse effects than conventional acute lymphoblastic leukemia (ALL) therapies, including chemotherapy or allogeneic HSCT. Conventional ALL therapies are associated with considerable health risks for patients; see e.g. Schmoll, Höffken, Possinger: Kompendium Internistische Onkologie, S. 2660 ff.; 4. Auflage, Springer Medizin Verlag Heidelberg).

2. Though allogeneic HSCT is currently considered to be the treatment of choice in adult Ph+ ALL, approximately one third of the transplanted patients relapse. Ph+ ALL patients carry the highest risk for a relapse among all patients within the ALL subtypes. As shown in the following examples, the administration of CD19×CD3 bispecific single chain antibody is especially appropriate for adult ALL patients with minimal residual disease (MRD). This accounts for minimal residual disease (MRD) defined by the Philadelphia chromosome translocation as well as for MRD defined by immunoglobulin or TCR rearrangement or t(4;11). Adult ALL patients, non-eligible for bone marrow transplantation, carrying t(4;11) or refractory Ph+ ALL patients have so far been considered incurable. The pharmaceutical methods and means of the invention therefore provide a therapeutic approach for the treatment, amelioration or elimination of MRD in adult ALL, thereby reducing or even abolishing the risk of a relapse for the patient. It is worth noting that, curative treatment for MRD-positive ALL patients has not yet been available until now.

3. In particular, the CD19×CD3 bispecific single chain antibody can be used for therapy of MRD-positive acute lymphoblastic leukemia (ALL) refractory to conventional ALL therapy, such as chemotherapy, administration of tyrosine kinase inhibitors, and/or HSCT.

4. Not only the CD19×CD3 bispecific single chain antibody can replace conventional acute lymphoblastic leukemia (ALL) therapies in patients non-eligible for allogeneic HSCT, it can also be used to convert ALL patients eligible for said transplantation into an MRD negative-status, as MRD-negative patients have a lower risk of relapse after transplantation than MRD-positive patients.

5. The high cytotoxic activity of the CD19×CD3 bispecific single chain antibody allows the elimination of leukemia cells in the bone marrow.

Acute lymphoblastic leukemia (ALL), including B-precursor acute lymphoblastic leukemia and other types of B (cell) lineage ALL, and treatments thereof are reviewed e.g. in Pui and Evans, N. Engl. J. Med. 354 (2006), 166-178; Hoelzer and Gökbuget; Hematology (2006); 133-141; or Apostolidou et al., Drugs 67 (2007), 2153-2171. Information with respect to ALL can also be found e.g. under http://www.cancer.gov, http://www.wikipedia.org or http://www.leukemia-lymphoma.org.

The term "bispecific single chain antibody" or "single chain bispecific antibody" or related terms in accordance with the present invention mean antibody constructs resulting from joining at least two antibody variable regions in a single polypeptide chain devoid of the constant and/or Fc portion(s) present in full immunoglobulins. A "linker" as used herein connects V domains of the same specificity, whereas a "spacer" as used herein connects V domains of different specificities. For example, a bispecific single chain antibody may be a construct with a total of two antibody variable regions, for example two VH regions, each capable of specifically binding to a separate antigen, and connected with one another through a short (usually less than 10 amino acids) synthetic polypeptide spacer such that the two antibody variable regions with their interposed spacer exist as a single contiguous polypeptide chain. Another example of a bispecific single chain antibody may be a single polypeptide chain with three antibody variable regions. Here, two antibody variable regions, for example one VH and one VL, may make up an scFv, wherein the two antibody variable regions are connected to one another via a synthetic polypeptide linker, the latter often being genetically engineered so as to be minimally immunogenic while remaining maximally resistant to proteolysis. This scFv is capable of specifically binding to a particular antigen, and is connected to a further antibody variable region, for example a VH region, capable of binding to a different antigen than that bound by the scFv. Yet another example of a bispecific single chain antibody may be a single polypeptide chain with four antibody variable regions. Here, the first two antibody variable regions, for example a VH region and a VL region, may form one scFv capable of binding to one antigen, whereas the second VH region and VL region may form a second scFv capable of binding to another antigen. Within a single contiguous polypeptide chain, individual antibody variable regions of one specificity may advantageously be separated by a synthetic polypeptide linker as described above, whereas the respective scFvs may advantageously be separated by a short polypeptide spacer as described above. Non-limiting examples of bispecific single chain antibodies as well as methods for producing them are shown in WO 99/54440, WO 2004/106381, WO 2007/068354, Mack, J. Immunol. (1997), 158, 3965-70; Mack, PNAS, (1995), 92, 7021-5; Kufer, Cancer Immunol. Immunother., (1997), 45, 193-7; Loffler, Blood, (2000), 95, 6, 2098-103; Brühl, J. Immunol., (2001), 166, 2420-2426.

As used herein, "CD3" denotes an antigen that is expressed on T cells, preferably human T cells as part of the multimolecular T cell receptor complex, the CD3 consisting of five different chains: CD3-epsilon, CD3-gamma, CD3-delta, CD3-eta and CD3 zeta. Clustering of CD3 on T cells e.g. by anti-CD3 antibodies leads to T cell activation similar to the binding of an antigen but independent from the clonal specificity of the T cell subset. Thus, the term "CD19×CD3 bispecific single chain antibody" as used herein relates to a CD3-specific construct capable of binding to the human CD3 complex expressed on human T cells and capable of inducing elimination/lysis of target cells, wherein such target cells carry/display an antigen which is bound by the other, non-CD3-binding portion of the bispecific single chain antibody. Binding of the CD3 complex by CD3-specific binders (e.g. a bispecific single chain antibody as administered according to the pharmaceutical means and methods of the invention) leads to activation of T cells as known in the art; see e.g. WO 99/54440 or WO 2007/068354. Accordingly, a construct appropriate for the pharmaceutical means and methods of the invention is advantageously able to eliminate/lyse target cells in vivo and/or in vitro. Corresponding target cells comprise cells expressing a tumor antigen, such as CD19, which is recognized by the second specificity (i.e. the non-CD3-binding portion of the bispecific single chain antibody) of the mentioned construct. Preferably, said second specificity is for human CD19 which has already been described in WO 99/54440, WO 2004/106381 or WO 2007/068354. According to this embodiment, each antigen-specific portion of the bispecific single chain antibody comprises an antibody VH region and an antibody VL region. An advantageous variant of this bispecific single chain antibody is from N terminus to C terminus:

$V_L(CD19)-V_H(CD19)-V_H(CD3)-V_L(CD3)$ (SEQ ID NO.: 1).

Within the meaning of the invention, the term "specifically binding" or related terms such as "specificity" is/are to be understood as being characterized primarily by two parameters: a qualitative parameter (the binding epitope, or where an antibody binds) and a quantitative parameter (the binding affinity, or how strongly this antibody binds where it does). Which epitope is bound by an antibody can advantageously be determined by e.g. FACS methodology, ELISA, peptide-spot epitope mapping, or mass spectroscopy. The strength of antibody binding to a particular epitope may advantageously be determined by e.g. known Biacore and/or ELISA methodologies. A combination of such techniques allows the calculation of a signal:noise ratio as a representative measure of binding specificity. In such a signal:noise ratio, the signal represents the strength of antibody binding to the epitope of interest, whereas the noise represents the strength of antibody binding to other, non-related epitopes differing from the epitope of interest. A signal:noise ratio of, for example at least 50, but preferably about 80 for a respective epitope of interest as determined e.g. by Biacore, ELISA or FACS may be taken as an indication that the antibody evaluated binds the epitope of interest in a specific manner, i.e. is a "specific binder". The term "binding to/interacting with" may also relate to a conformational epitope, a structural epitope or a discountinuous epitope consisting of two or even more regions of the human target molecules or parts thereof. A conformational epitope is defined by two or more discrete amino acid sequences separated in the primary sequence which come together on the surface of the molecule when the polypeptide folds to the native protein (Sela, (1969) Science 166, 1365 and Laver, (1990) Cell 61, 553-6). The term "discontinuous epitope" means non-linear epitopes that are assembled from residues from distant portions of the polypeptide chain. These residues come together on the surface of the molecule when the polypeptide chain folds into a three-dimensional structure to constitute a conformational/structural epitope.

The term "treatment" as used herein means in the broadest sense medical procedures or applications that are intended to relieve illness. In the present case, the administration of the CD19×CD3 bispecific single chain antibody (prepared for administration to an adult ALL patient) as described herein is for the treatment, amelioration or elimination of the ALL disease in adult patients.

The term "patient" as used herein refers to a human adult patient. The term "adult ALL" or "adult ALL patient" or "adult patient" as referred to herein denotes adults aged more than 18 years, i.e. patients aged 19, 20, 21, 22, 23, 24, 25, 30, 35, 40, or 50 years or more. Even patients with 70, 75, 80, 85, 90, 100 years or older may be treated by the methods and means of the invention. The indicated age is to be understood as the age of the adult at diagnosis of the ALL disease.

The term "amelioration" as used herein is synonymous with improvement. If an adult ALL patient's condition shows amelioration, the patient is clearly better—there is some improvement in her or his condition. For example, it may be an improvement in the ALL patient's condition, if a stabilization of the ALL disease can be achieved (also termed stable disease), i.e. the ALL disease is no longer progressive. Even better, MRD positive acute lymphoblastic leukemia (ALL) is converted into an MRD negative status.

The term "elimination" as used herein means the removal of leukemic cells from the body of an adult ALL patient. As shown in the following example, administration of the CD19×CD3 bispecific single chain antibody is able to convert MRD positive acute lymphoblastic leukemia (ALL) into an MRD negative status in various ALL subtypes.

The term "administration" as used herein means administration of a therapeutically effective dose of the aforementioned CD19×CD3 bispecific single chain antibody to an individual, i.e. a human patient. Preferably, the ALL patient is an adult patient, as defined herein.

By "therapeutically effective amount" is meant a dose that produces the effects for which it is administered, preferably the conversion of an minimal residual disease (MRD)-positive acute lymphoblastic leukemia (ALL) status into an MRD-negative ALL status. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The attending physician and clinical factors will determine the dosage regimen. As is well known in the medical arts, dosages for any one patient depends upon many factors, including the patient's size, body surface area, age, the particular compound to be administered, sex, time and route of administration, general health status, and other drugs being administered concurrently.

As is well known in the medical arts, dosages for any one patient depends upon many factors, including the adult patient's size, body surface area, age, the particular compound to be administered, sex, time and route of administration, general health status, and other drugs being administered concurrently. A typical dose can be, for example, in the ranges set forth in the embodiments of the invention and the appended examples; however, doses below or above this exemplary range are envisioned, especially considering the aforementioned factors.

The term "continuous infusion" refers to an infusion which is allowed to proceed permanently over a time period, i.e. without interruption. "Continuous infusion" refers to a permanently administered infusion. Accordingly, in the context of the invention, the terms "permanent" and "continuous" are used as synonyms. Within the meaning of the invention, e.g. the term "4 week continuous infusion" denote(s) a situation in which the CD19×CD3 bispecific single chain antibody used in the pharmaceutical means and methods according to the invention is continuously administered to the body of an adult patient over a period of 4 weeks in a sustained, constant fashion throughout the entire duration required in the pharmaceutical means and methods of the invention. Continuous administration schemes of the CD19×CD3 bispecific single chain antibody are described in more detail in WO 2007/068354. An interruption of the introduction of CD19×CD3 bispecific single chain antibody is avoided, that is to say a transition from a state in which this antibody is being administered to the body of the patient to a state in which this antibody is no longer being administered to the body of the patient does not, or does not significantly occur over the entire duration of administration required by the pharmaceutical means and methods of the invention for other reasons than replenishing the supply of CD19×CD3 bispecific single chain antibody being administered or medical interventions which become necessary and the like. In as far as such necessary replenishing leads to a temporary interruption of the introduction of the antibody administered, such administration is still to be understood as being "uninterrupted" or "permanent" in the sense of the pharmaceutical means and methods according to the invention. In most cases, such replenishing will generally be of such a short duration that the time during which antibody is not being introduced into the body of the patient will be vanishingly small when compared to the time planned for the overall administration regimen according to the pharmaceutical means and methods according to the invention. In accordance with the invention, one treatment cycle is to be understood as a 4-week continuous infusion of the CD19×CD3 bispecific single chain antibody to the adult ALL patient, followed by a 2-week treatment-free interval. It may be that upon MRD staging of the treated patient(s) after a 4 week-continuous administration or one treatment cycle, a minimal response or partial response to the bispecific single chain antibody treatment may be diagnosed. In this case, the continuous administration may be extended by additional one, two, three, four, five or even up to ten treatment cycles in order to achieve a better therapeutic result, e.g. stable disease or even a complete response. Preferably, said complete response is MRD-negativity. In an alternative embodiment, the 4-week continuous infusion of the CD19×CD3 bispecific single chain antibody to the adult ALL patient may be followed by allogeneic HSCT. It is also envisaged that a patient treated by one, two, three, four or even more treatment cycles as set forth above may receive an allogeneic HSCT transplantation thereafter.

As shown in the following example, 13 of 16 adult ALL patients became MRD negative upon treatment with the CD19×CD3 bispecific single chain antibody, which corresponds to an extraordinary complete molecular response rate of 81%. More specifically, in nine out of eleven patients with immunoglobulin or TCR rearrangements, one out of two patients with t(4; 11) translocations and three out of four patients with bcr/abl transcripts MRD-negativity could be achieved. Preferably, the major therapeutic goal of the administration of the CD19×CD3 bispecific single chain antibody, either alone or in combination with allogeneic HSCT, to an adult ALL patient is the conversion of an MRD-positive status into an MRD-negative status, as defined herein.

Continuing uninterrupted administration of the bispecific single chain antibody in the manner of the pharmaceutical means and methods according to the invention for longer periods of time allows the advantageous T cell activation mentioned in the examples to exert its effect for long enough to advantageously clear all diseased cells from the body. Since the rate of uninterruptedly administered bispecific single chain antibody is kept low, application of therapeutic agent may be continued longer without risk of deleterious side effects for the patient.

The CD19×CD3 bispecific single chain antibody as used herein is advantageously in the form of a pharmaceutical composition for administration to a human patient diagnosed with acute lymphoblastic leukemia (ALL). The human patient is preferably an adult as defined herein below. While the bispecific single chain antibody as used herein may be administered per alone, preferred is administration in a pharmaceutically acceptable carrier. Examples of suitable pharmaceutical carriers are well known in the art and include phosphate buffered saline solutions, water, liposomes, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Preparations for parenteral administration include sterile aqueous or non-aqueous solutions, or suspensions. Examples of non-aqueous solvents are propylene glycol, polyethylene glycol, and injectable organic esters such as ethyl oleate. Aqueous carriers include water, aqueous solutions, or suspensions, including saline and buffered media. Parenteral vehicles include sodium chloride solution, Ringer's dextrose, dextrose and sodium chloride, or lactated Ringer's. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the composition might comprise proteinaceous carriers, like, e.g., serum albumine or immunoglobuline, preferably of human origin. It is envisaged that the composition might comprise, in addition to the proteinaceous bispecific single chain antibody further biologically active agents, depending on the intended use of the pharmaceutical composition. Such agents might be agents acting as cytostatica, agents preventing hyperurikemia, agents inhibiting immune reactions (e.g. corticosteroids, FK506), drugs acting on the circulatory system and/or agents such as T-cell co-stimulatory molecules or cytokines known in the art.

Preferably, the CD19×CD3 bispecific single chain antibody as defined herein is formulated in a buffer, a stabilizer and a surfactant. The buffer may be a phosphate, citrate, succinate or acetate buffer. The stabilizer may be (an) amino acid(s) and/or a sugar. The surfactants may be detergents, PEGs, or the like. More preferably, the CD19×CD3 bispecific single chain antibody as defined herein is formulated in citrate, lysine, trehalose and Tween 80. As a diluent for the pharmaceutical composition of the invention, isotonic saline and Tween 80 is preferred.

Preferably, in the uses or methods of the invention, the pharmaceutical composition is to be administered to a human adult patient diagnosed with acute lymphoblastic leukemia (ALL).

The success of the CD19×CD3 bispecific single chain antibody therapy may be monitored by established standard methods for the respective disease entities: For B cell ALL therapy, Fluorescence Activated Cell Sorting (FACS), bone marrow aspiration and various leukemia specific clinical chemistry parameters and other established standard methods may be used. Methods and means for the determination of the minimal residual disease (MRD) status have been described above.

Cytotoxicity can be detected by methods known in the art and methods as illustrated e.g. in WO 99/54440, WO 2004/106381, WO 2007/068354: In a preferred embodiment, the acute lymphoblastic leukemia (ALL) of the adult patient(s) is refractory to chemotherapy, preferably refractory to chemotherapy with respect to MRD (i.e. the MRD in these ALL patients is resistant to chemotherapy). Even more preferred, the acute lymphoblastic leukemia (ALL) is refractory to chemotherapy in patients non-eligible for allogeneic HSCT.

The term "chemotherapy" as used herein denotes chemotherapy used for the treatment of acute lymphoblastic leukemia (ALL). Chemotherapy is the initial treatment of choice for ALL. Most ALL patients end up receiving a combination of different treatments. In the treatment of ALL, there are no surgical options, due to the body-wide distribution of the malignant cells. In general, cytotoxic chemotherapy for ALL combines multiple anti-leukemic drugs in various combinations. Chemotherapy for ALL consists of three phases: remission induction, intensification, and maintenance therapy. Chemotherapy is also indicated to protect the central nervous system from leukemia. The aim of remission induction is to rapidly kill most tumor cells and get the patient into remission.

This is defined as the presence of less than 5% leukemic blasts in the bone marrow (as determined by light microscopy), normal blood cells and absence of tumor cells from blood, and absence of other signs and symptoms of the disease. For example a combination of Prednisolone or dexamethasone (in children), vincristine, asparaginase, and daunorubicin (used in Adult ALL) is used to induce remission. Intensification uses high doses of intravenous multi-drug chemotherapy to further reduce tumor burden. Typical intensification protocols use vincristine, cyclophosphamide, cytarabine, daunorubicin, etoposide, thioguanine or mercaptopurine given as blocks in different combinations. Since ALL cells sometimes penetrate the Central Nervous System (CNS), most protocols include delivery of chemotherapy into the CNS fluid (termed intrathecal chemotherapy). Some centers deliver the drug through Ommaya reservoir (a device surgically placed under the scalp and used to deliver drugs to the CNS fluid and to extract CNS fluid for various tests). Other centers perform multiple lumbar punctures as needed for testing and treatment delivery. Intrathecal methotrexate or cytarabine is usually used for this purpose. The aim of maintenance therapy is to kill any residual cell that was not killed by remission induction, and intensification regimens. Although such cells are few, they will cause relapse if not eradicated. For this purpose, daily oral mercaptopurine, once weekly oral methotrexate, once monthly 5-day course of intravenous vincristine and oral corticosteroids are usually used. The length of maintenance therapy is 3 years for boys, 2 years for girls and adults. Central nervous system relapse is treated with intrathecal administration of hydrocortisone, methotrexate, and cytarabine (Hoffbrand et al., Essential Hematology, Blackwell, $5^{th}$ edition, 2006). As the chemotherapy regimens can be intensive and protracted (often about 2 years in case of the GMALL UKALL, HyperCVAD or CALGB protocols; about 3 years for males on COG protocols), many patients have an intravenous catheter inserted into a large vein (termed a central venous catheter or a Hickman line), or a Portacath (a cone-shaped port with a silicone nose that is surgically planted under the skin, usually near the collar bone).

Chemotherapy for ALL has been described e.g. in Schmoll, Höffken, Possinger (loc. cit.).

In light of the above, the term "refractory to chemotherapy" as used herein denotes resistance of the acute lymphoblastic leukemia cells to chemotherapy.

Patients can experience a recurrence of ALL after initial therapy and/or become refractory to chemotherapy following treatment. ALL patients who are refractory to chemotherapy have a markedly poor prognosis. In particular, the prognosis of adult patients with Ph+ ALL treated only with chemotherapy is poor, with a less than 10% probability of long-term survival. Since the pharmaceutical methods and means of the invention are capable of rendering the adult ALL patients MRD-negative, they are particularly useful for the treatment of ALL patients refractory to chemotherapy.

The term "allogeneic hematopoietic stem cell transplantation" as used herein means allogeneic hematopoietic stem cell transplantation (HSCT) or bone marrow transplantation (BMT) which is a medical procedure in the field of hematology and oncology that involves transplantation of hematopoietic stem cells (HSCs). It is most often conducted in patients with diseases of the lymph nodes, blood or bone marrow, such as ALL. Allogeneic HSCT is a procedure in which a person receives blood-forming stem cells (cells from which all blood cells develop) from a genetically similar, but not identical, donor. This is often a close relative, such as a mother, father, sister or brother, but could also be an unrelated donor. Most recipients of HSCTs are leukemia (e.g. ALL) patients who would benefit from treatment with high doses of chemotherapy or total body irradiation. However allogeneic HSCT remains a risky and toxic treatment.

The term "non-eligible for HSCT" as used herein means those adult patients for whom allogeneic HSCT is not the ALL treatment of choice, for instance, due to medical reasons. For example, it can be the case that no appropriate donor is available, or the patient has exceeded the upper age limit. As shown in the following example, all patients have been refractory to chemotherapy, or in case of Ph+ ALL also refractory or intolerant to tyrosine kinase before inclusion into the study. Eight patients treated with the CD19×CD3 bispecific single chain antibody have been non-eligible for allogeneic HSCT, such as for example patients 111-003, 108-002, 109-006 or 109-007.

So far, ALL meant the death sentence for patients refractory to chemotherapy and non-eligible for allogeneic HSCT. The pharmaceutical methods and means of the invention for the first time provide a therapy for this patient population in that it eliminates the minimal residual disease (MRD) which otherwise would cause a relapse and kill said patients.

In an alternative embodiment of the pharmaceutical methods and means of the invention, said method is followed by allogeneic hematopoietic stem cell transplantation or said method replaces allogeneic hematopoietic stem cell transplantation in adult patients eligible for allogeneic HSCT.

The term "eligible for allogeneic HSCT" as used herein means that allogeneic HSCT is the required therapy for the adult ALL patient. In cases, where the ALL patient is eligible for allogeneic HSCT, the following two scenarios may be envisaged. First, in one embodiment of the pharmaceutical methods and means of the invention, the administration of the CD19xCD3 bispecific single chain antibody (alone or preferably as a pharmaceutical composition) can be used to replace allogeneic HSCT used as a conventional therapy for adult ALL patients eligible for transplantation. So the pharmaceutical methods and means of the invention can avoid the health risks for the ALL patients associated with allogeneic hematopoietic stem cell transplantation. In addition, 30% of the transplanted ALL patients usually relapse after transplantation. So the pharmaceutical methods and means of the invention can be used to treat these patients. In an alternative embodiment, the continuous infusion of the CD19xCD3 bispecific single chain antibody to the adult ALL patient may be followed by an allogeneic hematopoietic stem cell transplantation. In this embodiment, the administration of a pharmaceutical composition comprising the CD19xCD3 bispecific single chain antibody construct can be used to convert ALL patients eligible for transplantation into an MRD negative-status before they receive the transplantation. So, the pharmaceutical methods and means of the invention can be used in order to eliminate MRD, which leads to a lower risk of relapse than the transplantation treatment of MRD-positive patients. The example presents a patient who has first been converted into an MRD-negative status upon treatment with the CD19xCD3 bispecific single chain antibody, followed by an allogeneic transplantation. So far, this patient is still MRD negative, with duration of MRD-negativity of 47 weeks until to date.

It is also within the scope of the pharmaceutical methods and means of the invention, that the CD19xCD3 bispecific single chain antibody construct be administered to adult ALL patients who have received an allogeneic HSCT and relapse thereafter.

In another preferred embodiment, the pharmaceutical methods and means of the invention are for the treatment, amelioration or elimination of minimal residual disease (MRD) in an adult patient with acute lymphoblastic leukemia (ALL).

The term "minimal residual disease (MRD)" as defined herein denotes a disease status after treatment e.g. with chemotherapeutics when leukemia cells cannot be found any longer in the bone marrow by light microscopic methods. More sensitive tests such as flow cytometry (FACS based methods) or polymerase chain reaction (PCR) have to be used in order to find evidence that leukemia cells remained in the bone marrow of the ALL patient. More specifically, the presence of leukemia cells below the cytological detection limit (5% leukemic cells) is defined as minimal residual disease (MRD). If no MRD is detectable ($<10^{-4}$, i.e. less than 1 leukemia cell per $10^4$ bone marrow cells detectable), a complete molecular remission is reached. A "MRD positive status" as defined herein means a bcr/abl signal or t(4;11) signal above detection limit and/or by individual rearrangements of immunoglobulin or T-cell receptor (TCR) genes above 10-4. A "MRD negative status" as defined herein means a bcr/abl signal or a t(4;11) translocation signal below detection limit or by individual rearrangements of immunoglobulin or T-cell receptor (TCR) genes below $10^{-4}$. The MRD status can be measured by PCR or FACS analysis in that the individual rearrangements of immunoglobulin genes or T-cell receptor (TCR) rearrangements, or bcr/abl fusion transcripts, or t(4;11) are quantitatively detected. For example, PCR analysis can detect fusion transcripts such as bcr/abl, or t(4;11) translocations and individual clonal rearrangements of immunoglobulins (IgH) and/or T-cell receptor genes (TCR).

Recurrent chromosomal abnormalities in the malignant cells of patients with acute lymphoblastic leukemia are hallmarks of the disease (Harrison and Foroni, Rev. Clin. Exp. Hematol. 6 (2002), 91-113). Specific aberrations which are frequently indicative of consistent underlying molecular lesions can assist or even establish the diagnosis and determine optimal therapy. In childhood ALL, numerous good and high-risk cytogenetic subgroups have been identified which are regularly used to stratify patients to particular therapies (Pui and Evans, N. Engl. J. Med. 354 (2006), 166-178). However, in adult ALL the role of cytogenetics in patient management has largely been centered on the presence of the Philadelphia (Ph) chromosome which usually arises from t(9;22)(q34;q11.2) and results in BCR-ABL (bcr/abl) fusion (Faderl et al., Blood 91 (1998), 3995-4019). Although the overall incidence of Ph+ ALL in adults is approximately 25%, it is correlated with age and rises to greater than 50% among patients older than the age of 55 years (Appelbaum, American Society of Clinical Oncology 2005 education book. Alexandria: ASCO, 2005: 528-532). Other cytogenetic translocations associated with specific molecular genetic abnormalities in acute lymphoblastic leukemia (ALL) are shown in Table 1.

TABLE 1

| Cytogenetic translocation | Molecular genetic abnormality |
| --- | --- |
| t(9; 22)(q34; q11) | BCR-ABL fusion(P185) |
| t(12; 21)CRYPTIC | TEL-AML1 fusion |
| t(1; 19)(q23; p13) | E2A-PBX fusion |
| t(4; 11)(q21; q23) | MLL-AF4 fusion |
| t(8; 14)(q24; q32) | IGH-MYC fusion |
| t(11; 14)(p13; q11) | TCR-RBTN2 fusion |

Cytogenetics, has been increasingly recognized as an important predictor of outcome in ALL (Moormann et al., Blood 109 (2007), 3189-97).

Some cytogenetic subtypes have a worse prognosis than others. These include e.g.:

(i) A translocation between chromosomes 9 and 22, the Philadelphia chromosome (Ph+), occurs in about 20% of adult and 5% in pediatric cases of ALL.

(ii) A translocation between chromosomes 4 and 11 occurs in about 4% of cases and is most common in infants under 12 months.

Rearrangements of immunoglobulin genes or T-cell receptor (TCR) rearrangements and their role in ALL have been described in the art (see e.g. Szczepański et al., Leukemia 12 (1998), 1081-1088).

In another preferred embodiment of the pharmaceutical methods and means of the invention, said adult patient is MRD-positive in complete hematological remission.

The term "remission" or "hematological remission" as used herein is to be understood as having no evidence of disease after treatment, e.g. after chemotherapy or transplantation. This means that the bone marrow contains fewer than 5% blast cells as determined by light microscopy, the blood cell counts are within normal limits, and there are no signs or symptoms of the ALL disease. A molecular complete remission means there is no evidence of leukemia cells in biopsies of the bone marrow, even when using very sensitive tests such as PCR. Put in other words: If no MRD is detectable (<$10^{-4}$, i.e. <1 leukemia cell per $10^4$ bone marrow cells), a complete molecular remission is reached.

After complete remission of the leukemia lesion(s) in a human adult ALL patient by chemotherapeutic treatment or allogeneic hematopoietic stem cell transplantation it may be the case that not all leukemia cells could be eliminated from the body. However, these remaining tumor cells may give rise to recurrent leukemia. The pharmaceutical means and methods of the invention can be used to kill these remaining tumor cells in order to prevent recurrence of the leukemia (originating from the occult leukemia cells remaining in the body after primary therapy). In this way, the pharmaceutical means and methods help to prevent disease relapse in adult ALL patients.

In another preferred embodiment of the pharmaceutical methods and means of the invention, the administration of said pharmaceutical composition converts MRD positive acute lymphoblastic leukemia (ALL) into an MRD negative status.

In another preferred embodiment of the pharmaceutical methods and means of the invention, MRD is measured with quantitative detection of individual rearrangements of immunoglobulin genes or T-cell receptor (TCR) rearrangements, or by bcr/abl fusion transcripts, or t(4;11) using PCR or FACS analysis.

As shown in the following examples, the administration of CD19×CD3 bispecific single chain antibody is especially appropriate for adult patients with minimal residual disease (MRD). This accounts for minimal residual disease (MRD) defined by the Philadelphia chromosome translocation or t(4;11) as well as for MRD defined by immunoglobulin or TCR rearrangements. The pharmaceutical methods and means of the invention therefore provide a therapeutic approach for the treatment, amelioration or elimination of MRD, thereby reducing or even abolishing the risk of relapse for the adult patient. Notably, curative treatment of MRD in ALL patients has not yet been available so far.

In another preferred embodiment of the pharmaceutical methods and means of the invention, said patient shows a bcr/abl signal or a t(4;11) signal above detection limit and/or at least one marker by rearrangement with a sensitivity of ≥$10^{-4}$.

The term "bcr/abl signal or t(4;11) translocation signal above detection limit" as used herein means that PCR or FACS analysis leads to a detectable bcr/abl signal or t(4;11) signal.

In another preferred embodiment of the pharmaceutical methods and means of the invention, the time to molecular relapse (detectable by the assays described above) is more than 4 months.

The term "molecular relapse" as used herein means that said patient shows a bcr/abl or t(4;11) translocation signal above detection limit and/or at least one marker by rearrangement with a sensitivity of ≥$10^{-4}$.

The term "with a sensitivity of ≥$10^{-4}$" as used herein means one or more than one leukemia cell(s) can be detected in 10.000 cells, in particular bone marrow cells.

In another preferred embodiment of the pharmaceutical methods and means of the invention, the corresponding variable heavy chain regions ($V_H$) and the corresponding variable light chain regions ($V_L$) regions in said CD19×CD3 bispecific single chain antibody construct are arranged, from N-terminus to C-terminus, in the order, $V_L$(CD19)-$V_H$(CD19)-$V_H$(CD3)-$V_L$(CD3).

The corresponding variable heavy chain regions ($V_H$) and the corresponding variable light chain regions ($V_L$) regions of the CD3 and CD19 binding domains of the CD19×CD3 bispecific single chain antibody are shown in SEQ ID NOs. 3 to 10, respectively. The corresponding CDR regions of the respective VH and VL regions of the mentioned CD19×CD3 bispecific single chain antibody are shown in SEQ ID NOs. 11 to 22.

In another preferred embodiment of the pharmaceutical methods and means of the invention, said CD19×CD3 bispecific single chain antibody construct comprises an amino acid sequence as set forth in SEQ ID NO. 1, or an amino acid sequence at least 90%, preferably at least 95% identical to SEQ ID NO. 1.

The invention describes a bispecific single chain antibody molecule comprising an amino acid sequence as depicted in SEQ ID NO. 1, as well as an amino acid sequence at least 90% or preferably 95% identical, most preferred at least 96, 97, 98, or 99% identical to the amino acid sequence of SEQ ID NO. 1. The invention describes also the corresponding nucleic acid sequence as depicted in SEQ ID NO. 2 as well as a nucleic acid sequence at least 90%, preferably 95% identical, most preferred at least 96, 97, 98, or 99% identical to the nucleic acid sequence shown in SEQ ID NO. 2. It is to be understood that the sequence identity is determined over the entire nucleotide or amino acid sequence. Moreover, it is to be understood that a bispecific single chain antibody molecule comprising an amino acid sequence at least 90% or preferably 95% identical, most preferred at least 96, 97, 98, or 99% identical to the amino acid sequence of SEQ ID NO. 1 contains all of the CDR sequences shown in SEQ ID NOs. 11 to 22. For sequence alignments, for example, the programs Gap or BestFit can be used (Needleman and Wunsch J. Mol. Biol. 48 (1970), 443-453; Smith and Waterman, Adv. Appl. Math 2 (1981), 482-489), which is contained in the GCG software package (Genetics Computer Group, 575 Science Drive, Madison, Wis., USA 53711 (1991). It is a routine method for those skilled in the art to determine and identify a nucleotide or amino acid sequence having e.g. 90%, 95%, 96%, 97%, 98% or 99% sequence identity to the nucleotide or amino acid sequences of the CD19×CD3 bispecific single single chain antibody described herein. For example, according to Crick's Wobble hypothesis, the 5' base on the anti-codon is not as spatially confined as the other two bases, and could thus have non-standard base pairing. Put in other words: the third position in a codon triplet may vary so that two triplets which differ in this third position may encode the same amino acid residue. Said hypothesis is well known to the person skilled in the art (see e.g. http://en.wikipedia.org/wiki/Wobble_Hypothesis; Crick, J Mol Biol 19 (1966): 548-55).

In another preferred embodiment of the pharmaceutical methods and means of the invention, one treatment cycle is a 4-week continuous infusion, followed by repeated cycles after a 2-week treatment-free interval or by an allogeneic hematopoietic stem cell transplantation.

In another preferred embodiment of the pharmaceutical methods and means of the invention, the treatment cycle is repeated at least three times, preferably four, five, six, seven or even up to ten times after determination of a MRD negative status (consolidation).

In another preferred embodiment of the pharmaceutical methods and means of the invention, the bispecific single chain antibody construct is to be administered in a daily dose of 10 μg to 100 μg per square meter patient body surface area.

As used herein, a dose range which is defined as "X to Y" equates with a dose range which is defined as "between X and Y". The range includes the upper limit and also the lower limit. This means that for example a daily dose of 10 μg to 100 μg per square meter patient body surface area includes "10 μg" and "100 μg".

In an even more preferred embodiment of the pharmaceutical methods and means of the invention, the CD19× CD3 bispecific single chain antibody construct is to be administered in a daily dose of 15 μg, 30 μg, 60 μg or 90 μg per square meter patient body surface area. Even more preferred, said antibody is to be administered in a daily dose of 15 to 30 μg per square meter patient body surface area, most preferred in a daily dose of 15 or 30 μg per square meter patient body surface area.

The average body surface area of an adult patient is hereby calculated in the context of the pharmaceutical method or use according to the invention to be in a range of 1.7 to 2.2 m².

Advantageously, the pharmaceutical composition comprising the CD19×CD3 bispecific single chain antibody as described herein further comprises, optionally (a) reaction buffer(s), storage solutions and/or remaining reagents or materials required for the recited method or use. Furthermore, said components can be packaged individually in vials or bottles or in combination in containers or multicontainer units.

In order to evaluate safety and tolerability of the CD19× CD3 bispecific single chain antibody as described herein, the compound is to be administered by long-term continuous infusion.

It has been found that the beneficial and unexpected effects of the pharmaceutical means and methods of the invention can be obtained by administering the CD19×CD3 bispecific single chain antibody in a daily dose of 10 microgram to 100 microgram per square meter body surface area. The daily dose may be kept constant over the administration period. However, it is also within the ambit of this embodiment that for the initial day(s) of the infusion period a lower dose of bispecific single chain antibody be administered ("initial dose") prior to the pharmaceutical methods described herein, whereas for the remaining infusion period a higher dose ("maintenance dose") be applied. For example, 5 microgram of bispecific single chain antibody per square meter body surface area may be administered at the first day(s) of the infusion period followed by administration of 15 microgram per square meter body surface as daily dose for the remaining treatment period. Or 15 microgram of bispecific single chain antibody per square meter body surface area may be administered at the first day(s) of the infusion period followed by administration of 30 or 45 microgram per square meter body surface as daily dose for the remaining treatment period. The initial dose may be administered for one, two or more days or even for one week (seven days). It is also envisaged that 5 microgram of bispecific single chain antibody per square meter body surface area may be administered at the first day(s) of the infusion period, followed by administration of 15 microgram per square meter body surface area at the following day(s) of the infusion period, followed by administration of 45 microgram per square meter body surface as daily (maintenance) dose for the remaining treatment period. The average body surface area of an adult patient is hereby calculated in the context of the pharmaceutical method or use according to the invention to be in a range of 1.7 to 2.2 m².

In another embodiment of the methods and uses of the invention, the dose is escalated after the first or further treatment cycles, for example from 15 to 30 or 60 or even 90 microgram/m²/24 hr.

The uninterrupted administration of the CD19×CD3 bispecific single chain antibody may be intravenous, parenteral, subcutaneous, transdermal, intraperitoneal, intramuscular or pulmonary. The intravenous mode of administration will in most cases be the mode of choice for uninterruptedly administering the CD19×CD3 bispecific single chain antibody and, as the case may be, for co-administration of a pharmaceutical agent as part of a regimen of co-therapy. As such, intraveneous administration is especially preferred. In this case, a suitable metering device such as the multitherapy infusion pump model 6060 manufactured by Baxter may advantageously be chosen. Whatever metering device is chosen, it should be of such design and construction as to minimize or, better, preclude an interruption of administration of therapeutic agent in the event of cartridge exchange and/or power cell replacement or recharging. This may be accomplished, for example by choosing a device with a secondary reservoir of CD19×CD3 bispecific single chain antibody solution apart from the cartridge to be exchanged so that continuous infusion from this secondary reservoir into the patient may continue even while the empty or almost empty cartridge is removed and replaced with a fresh one.

A mode of intravenous administration and, as the case may be, of co-administration as part of a regimen of co-therapy involves the implantation of a pump into the body of the patient for metering such administration. One of ordinary skill in the art is aware of such metering pumps, for example model 6060 manufactured by Baxter as set forth above.

As a non-limiting example, it may be that the uninterrupted, i.e. continuous administration is to be realized by a small pump system worn by or implanted into the patient for metering the influx of therapeutic agent into the body of the patient. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention to together make up one "uninterrupted administration" of such therapeutic agent. The same would apply for very long administrations in which the cartridge would require replacement more than once, or in which the power cells driving the pump would require replacement, leading to a temporary offset of the flow of therapeutic solution into the body of the patient.

Appropriate measures should also be taken to minimize the danger of infection at the puncture site of administration into the patient's body, as such long-term wounds are especially prone to such infection. The above also applies for intramuscular administration via a similar delivery system.

The continuous administration may be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

In a further preferred embodiment, the continuous administration is accomplished via a pulmonary route, for example via a tube worn in one or both nostrils of the nose, the tube being connected to a pressurized tank, the content of which is precisely metered.

Furthermore, the invention relates to a CD19×CD3 bispecific single chain antibody construct for the treatment, amelioration or elimination of adult acute lymphoblastic leukemia (ALL). The invention further relates to the use of a CD19×CD3 bispecific single chain antibody construct for the preparation of a pharmaceutical composition for the treatment, amelioration or elimination of adult acute lymphoblastic leukemia (ALL). Preferably, said acute lymphoblastic leukemia (ALL) is B-lineage acute lymphoblastic leukemia, more preferably B-precursor acute lymphoblastic leukemia.

In a preferred embodiment of the mentioned medical uses, said acute lymphoblastic leukemia (ALL) is refractory to chemotherapy in patients non-eligible for allogeneic HSCT.

In an alternative embodiment of the mentioned medical uses, the administration of the CD19×CD3 bispecific single chain antibody construct is followed by allogeneic HSCT or said uses replace allogeneic HSCT in patients eligible for allogeneic HSCT In another preferred embodiment of the mentioned medical uses, the CD19×CD3 bispecific single chain antibody construct is for the treatment, amelioration or elimination of minimal residual disease (MRD) in a patient with acute lymphoblastic leukemia (ALL). Preferably, said patient is MRD-positive in complete hematological remission.

In a further preferred embodiment of the mentioned medical uses, the administration of said CD19×CD3 bispecific single chain antibody results in stable disease or converts MRD positive acute lymphoblastic leukemia (ALL) into an MRD negative status.

Preferably, MRD is measured with quantitative detection of individual rearrangements of immunoglobulin genes or T-cell receptor (TCR) rearrangements, or by bcr/abl fusion transcripts, or t(4;11), using PCR or FACS analysis.

Even more preferred, the ALL patient shows a bcr/abl or a t(4;11) signal above detection limit and/or at least one marker by rearrangement with a sensitivity of $\geq 10^{-4}$.

In another preferred embodiment of the mentioned medical uses, the time to molecular relapse detectable by the indicated detection methods is more than 4 months.

In another preferred embodiment of the mentioned medical uses, the corresponding variable heavy chain regions ($V_H$) and the corresponding variable light chain regions ($V_L$) regions in said CD19×CD3 bispecific single chain antibody construct are arranged, from N-terminus to C-terminus, in the order, $V_L$(CD19)-$V_H$(CD19)-$V_H$(CD3)-$V_L$(CD3).

Preferably, said CD19×CD3 bispecific single chain antibody construct comprises an amino acid sequence as set forth in SEQ ID NO. 1, or an amino acid sequence at least 90%, preferably 95% identical to SEQ ID NO. 1.

In a further preferred embodiment of the mentioned medical uses, one treatment cycle is a 4-week continuous infusion, followed by repeated cycles after a 2-week treatment-free interval.

Preferably, the treatment cycle is repeated at least three times, after determination of a MRD negative status (consolidation).

In another preferred embodiment of the mentioned medical uses, the CD19×CD3 bispecific single chain antibody construct is to be administered in a daily dose of 10 µg to 100 µg per square meter patient body surface area.

Preferably, the CD19×CD3 bispecific single chain antibody construct is to be administered in a daily dose of 15 µg to 30 µg per square meter patient body surface area.

The definitions and explanations provided with respect to the pharmaceutical methods and means of the invention apply mutatis mutandis to the medical uses of the CD19×CD3 bispecific single chain antibody construct described herein.

The Figures show:

FIG. 1: CD19×CD3 bispecific single chain antibody mode of action. CD19×CD3 bispecific single chain antibody (blinatumomab or MT103) redirects CD3-positive cytotoxic T cells to eliminate human acute lymphoblastic leukemia cells carrying the CD19 antigen.

Figure 2:
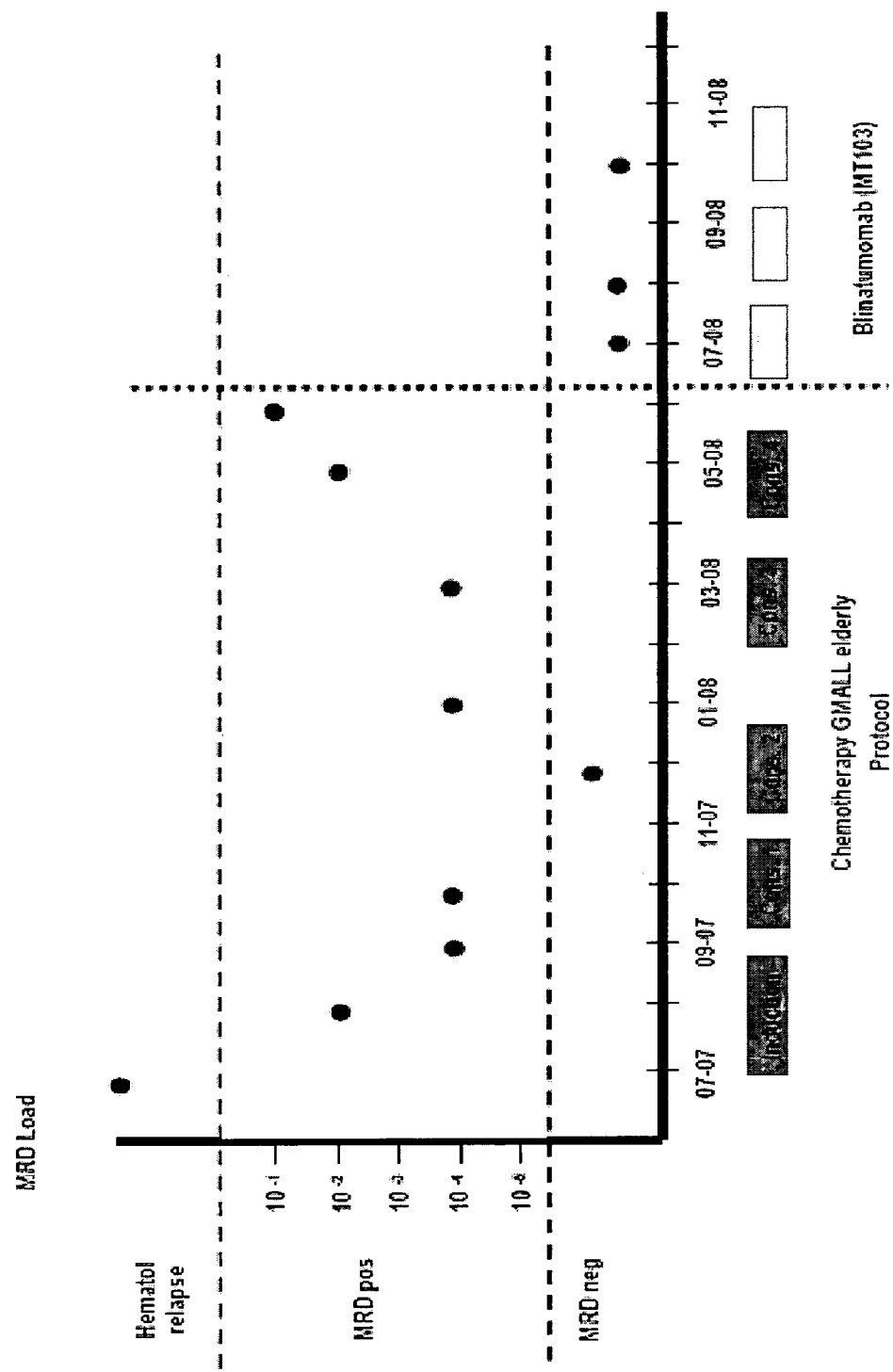

FIG. 2: Example of minimal residual disease (MRD) course. PCR based measurement of TCR rearrangement (MRD) in common acute lymphoblastic leukemia (cALL) patient 109-002 shows an MRD positivity before treatment with CD19×CD3 bispecific single chain antibody and ongoing MRD negativity starting after the 1st cycle CD19×CD3 bispecific single chain antibody.

Figure 3:
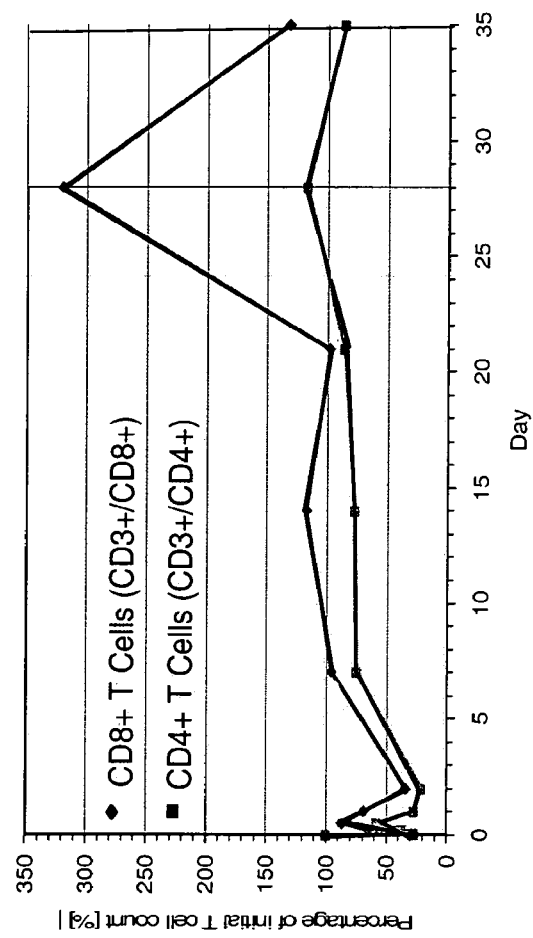

FIG. 3: T cell kinetics of CD4 and CD8 T cells of patient 109-002 during treatment cycle 1. Representative example of pharmacodynamics, showing rapid redistribution of T cells and an increase mainly in the number of cytotoxic CD8 T cells.

Figure 4:
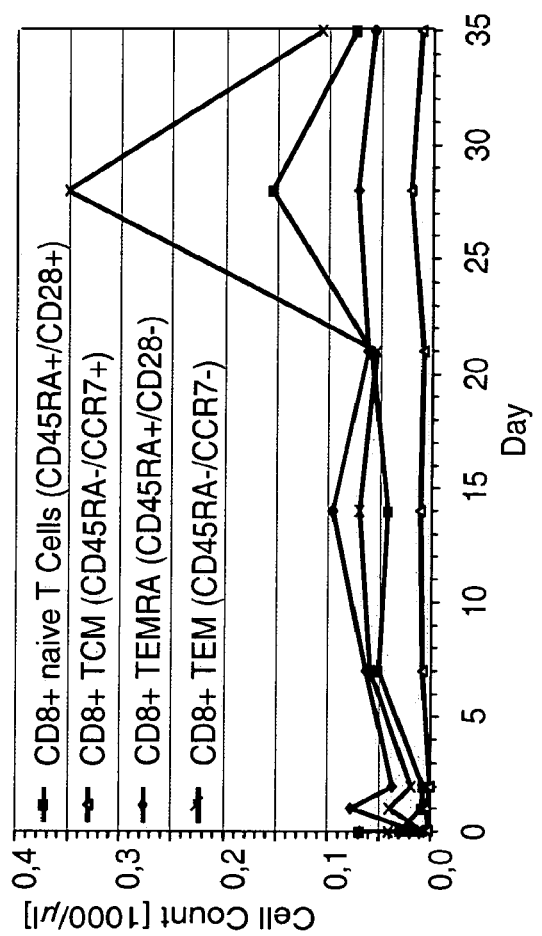

FIG. 4: T cell kinetics of T cell subsets of patient 109-002 during treatment cycle 1. Representative example of pharmacodynamics, showing rapid redistribution of T cells and expansion of T effector memory cells (TEM). Naive T cells are not expanded.

FIG. 5: The first four patients who have been enrolled in the phase II study. All patients had previously received standard chemotherapy regimens for ALL according to GMALL protocols including at least one consolidation treatment.

FIG. 6: Minimal residual disease (MRD) responses in the indicated ALL patients (i.e. the first four patients enrolled in the phase II study) after the first treatment cycle with CD19×CD3 bispecific single chain antibody.

FIG. 7: Update on minimal residual disease (MRD) responses. In nine out of eleven patients with immunoglobulin or TCR rearrangements, in one out of two patients with t(4;11) translocations and in three out of four patients with bcr/abl transcripts, MRD-negativity could be achieved. In sum, 13 of 16 evaluable patients (81%) became MRD negative.

Figure 8:
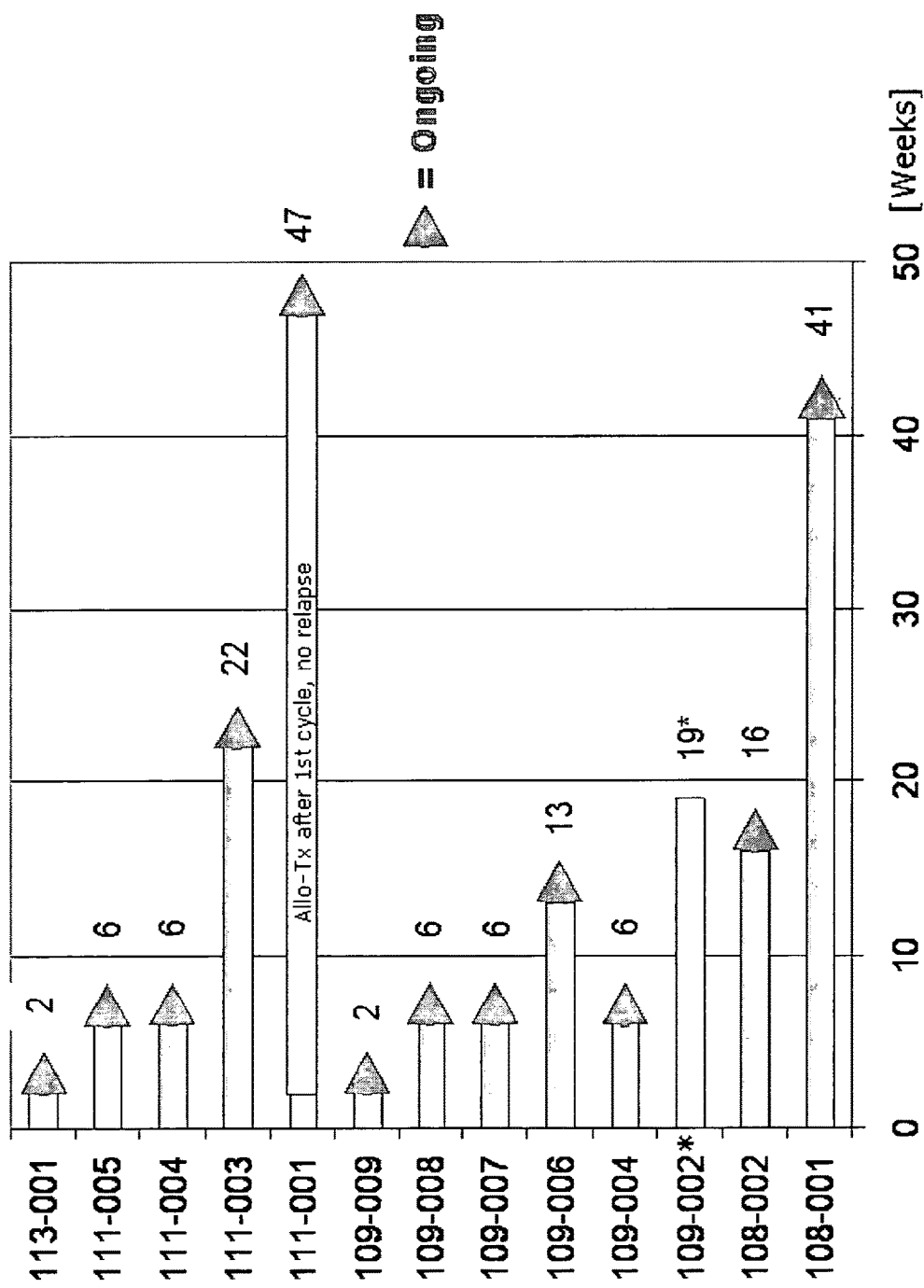

FIG. 8: Duration of minimal residual disease (MRD)-negativity (status as of 25 May 2009). The longest duration of MRD-negativity observed so far in patient 108-001 having not received a transplantation after the antibody treatment is 41 weeks. Patient 111-001 with MRD-negativity from 23 Jun. 2008 to 27 Oct. 2008 after CD19×CD3 bispecific single chain antibody-treatment and having received a successful allogeneic hematopoietic stem cell transplantation thereafter is relapse-free to date. The arrowhead means that the response is still ongoing (status May 25, 2009). Patient 109-002 (*) had a testicular relapse followed by hematological relapse after 19 weeks of MRD-negativity.

The invention is further illustrated by the following example:

EXAMPLE

1. The generation, expression and cytotoxic activity of the CD19×CD3 bispecific single chain antibody has been described in WO 99/54440. The corresponding amino and nucleic acid sequences of the CD19×CD3 bispecific single chain antibody are shown in SEQ ID NOs. 1 and 2, respectively. The VH and VL regions of the CD3 binding domain of the CD19×CD3 bispecific single chain antibody are shown in SEQ ID NOs. 7 to 10, respectively, whereas the VH and VL regions of the CD19 binding domain of the CD19×CD3 bispecific single chain antibody are shown in SEQ ID NOs 3 to 6, respectively. The corresponding CDR regions are shown in SEQ ID NOs. 11 to 22.

2. An ongoing phase 1 trial in relapsed B-NHL patients shows high response rate at 60 μg/m²/day of CD19×CD3 bispecific single chain antibody. Responses have a duration of up to more than 12 months (ongoing in several patients). Removal of bone marrow infiltrating B-NHL cells started at 15 μg/m²/day (Bargou et al., Science 2008).

3. Based on these results, a phase II dose-escalating study was designed in collaboration with the German Multicenter Study Group on Adult Acute Lymphoblastic Leukemia (GMALL) to investigate efficacy, safety, and tolerability of the CD19×CD3 bispecific single chain antibody in adult (non-transplanted) acute lymphoblastic leukemia (ALL) patients who achieved a complete hematological remission, but remained minimal residual disease (MRD)-positive. MRD is an independent prognostic factor that reflects primary drug resistance and is associated with a high relapse risk after start of consolidation. This applies for Ph+/BCR-ABL-positive and -negative ALL. MRD was measured with standardized methods either by quantitative detection of individual rearrangements of immunoglobulin or T-cell receptor (TCR) rearrangements, or by bcr/abl fusion transcripts or t(4;11) translocations. The study population includes adult patients with acute B-precursor acute lymphoblastic leukemia (ALL) who show a bcr/abl or t(4; 11) translocation signal above detection limit and/or at least one marker by rearrangement with a sensitivity of $\geq 10^{-4}$. More specifically, the major inclusion criteria included:

B-precursor ALL patients in complete hematological remission with molecular failure or molecular relapse starting at any time after consolidation 1 of front-line therapy within standard protocols.

Patients must have a molecular marker for evaluation of minimal residual disease which is either bcr/abl or t(4;11) translocation at any detection level or individual rearrangements of immunoglobulin or TCR-genes measured by an assay with a sensitivity of minimum $10^{-4}$ and quantitative range to $10^{-4}$ for at least one marker.

Primary endpoint of the (ongoing) phase II study is the conversion rate to minimal residual disease (MRD) negative status as defined by a bcr/abl or t(4;11) translocation signal below detection limit and/or by detection of individual rearrangements of immunoglobulin or T-cell receptor (TCR) genes below $10^{-4}$. Secondary endpoints are time to hematological relapse, time to MRD progression, and time to molecular relapse. One treatment cycle of the CD19×CD3 bispecific single chain antibody is a 4-week continuous intravenous infusion, which can be followed by allogeneic hematopoietic stem cell transplantation after the first cycle or further cycles, or by repeated cycles after a 2-week treatment-free interval. Minimal residual disease (MRD) status is controlled after each treatment cycle. The starting dose level is 15 microgram/m²/24 hr, which may be escalated to 30 microgram/m²/24 hr and higher dose levels (60 microgram/m²/24 hr or 90 microgram/m²/24 hr) based on clinical activity and safety data. For statistical design, Simon's MinMax two stage design (14 to 21 patients) is being used.

In the following, the data of the first four patients enrolled in the study are presented exemplarily in more detail. These four patients aged 31, 57, 62, and 65 years received the initial dose level of 15 microgram/m²/24 hr. As shown in FIG. 5, patient nos. 111001, 109002 and 110002 have been diagnosed with c-ALL, whereas patient no. 108001 is a pre-B-ALL patient. The four patients had previously received standard chemotherapy regimens for ALL according to GMALL protocols including at least one consolidation treatment. All of them have been refractory to chemotherapy as regards minimal residual disease (MRD). More specifically, all patients have been MRD-positive in complete hematological remission. Patients nos. 110002, 108001 and 109002 have been non-eligible for allogeneic hematopoietic stem cell transplantation, whereas patient no. 111001 has been eligible for said transplantation.

As shown in FIG. 6, three out of the first 4 patients enrolled in the study had minimal residual disease (MRD) by immunoglobulin or TCR rearrangements at levels of $10^{-4}$ (patient no. 111001), $10^{0.3}$ (patient no. 108001) and $10^{-1}$ (patient no. 109002), and one patient (patient no. 110002) had MRD by bcr/abl fusion transcripts at a level of $10^{-4}$. Three out of the 3 patients, i.e. patient nos. 111001, 108001 and 109002 with immunoglobulin or TCR rearrangements turned MRD negative after the first treatment cycle, independently from the level of MRD positivity at baseline. Patient no. 111001, the only one of the four patients eligible for allogeneic hematopoietic stem cell transplantation, received a transplantation after having been converted into MRD negativity upon CD19×CD3 bispecific single chain antibody treatment.

FIG. 2 provides an example of the minimal residual disease (MRD) course in patient 109002. PCR based measurement of TCR rearrangement (MRD) in common acute lymphoblastic leukemia (cALL) patient 109002 shows an MRD positivity before treatment with CD19×CD3 bispecific single chain antibody (Blinatumomab) and MRD negativity starting after the 1st cycle CD19×CD3 bispecific single chain antibody and lasting until week 19. Thereafter, the patient had a testicular relapse, followed by a haematological relapse.

The other patient having no. 110002 had stable bcr/abl level without signs of hematological relapse after the initial treatment cycle; see FIG. 6.

The treatment of the patients with CD19×CD3 bispecific single chain antibody was well tolerated: Except for fever on the first 3 days of treatment, no clinically significant toxicities were recorded.

Meanwhile, seventeen adult patients have been treated, or are still on treatment with the CD19×CD3 bispecific single chain antibody, up to date. All patients have been refractory to conventional ALL therapies, including chemotherapy, before the antibody treatment. None of them has received an allogeneic hematopoietic stem cell transplantation before the antibody treatment. The median age of the patients was 48 years, ranging from 20 to 77 years. Ten of the patients were female, seven were male patients. 14 patients received the dose level of 15 microgram/m²/24 hr of CD19×CD3 bispecific single chain antibody, whereas in three patients the dose has been escalated from 15 to 30 microgram/m²/24 hr after the first or further treatment cycles: in patient 109-004 the dose escalation was carried out after the second treatment cycle (with a total of three treatment cycles, followed by allogeneic hematopoietic stem cell transplantation), in patient 109-003 after the third treatment cycle (with a total of four treatment cycles), and in patient 110-002 after the sixth treatment cycle (with a total of seven treatment cycles). Eleven of these patients had minimal residual disease (MRD) by immunoglobulin or TCR rearrangements, two patients had t(4;11) translocations and four patient had bcr/abl fusion transcripts.

As a result, MRD response was evaluable in 16 of 17 patients. As shown in FIG. 7, 13 of 16 evaluable patients became MRD negative, which corresponds to an extraordinary complete molecular response rate of 81%. More specifically, in nine out of eleven patients with immunoglobulin or TCR rearrangements, one out of two patients with t(4;11) translocations and three out of four patients with bcr/abl transcripts MRD-negativity could be achieved. As shown in FIG. 8, the longest duration of MRD-negativity in patient 108-001 having not received a transplantation after the antibody treatment observed so far is 41 weeks. Another patient with MRD-negativity from 23 Jun. 2008 to 27 Oct. 2008 and having received a successful allogeneic hematopoietic stem cell transplantation after the antibody treatment is relapse-free to date; see patient 111-001 in FIG. 8. Remarkably, the bcr/abl patients who could successfully be treated with the CD19×CD3 bispecific single chain antibody were refractory or intolerant to tyrosine kinase inhibitors imatinib and/or dasatinib in previous ALL treatment regimen. In particular, one of the bcr/abl responders to treatment with CD19×CD3 bispecific single chain antibody had a T315I mutation which is refractory to therapy by tyrosine kinase inhibitors. Thus, the administration of the CD19×CD3 bispecific single chain antibody now provides for the first time for a therapy for dasatinib-refractory ALL patients with bcr/abl transcripts. Only three out of a total of 17 patients did not become MRD negative. However, in two of them stable disease could be achieved. Only one patient with initial stable disease had a hematological relapse in the third treatment cycle. One patient was not evaluable due to an SAE on study day 2.

In summary, an absolutely exceptional complete molecular response rate of 81% could be achieved in patients with B-precursor ALL upon treatment with CD19×CD3 bispecific single chain antibody. Activity of the mentioned antibody could be observed in all patients subsets treated, including tyrosine kinase inhibitors-refractory (T315I) bcr/abl patients and patients with t(4;11) translocations. In addition, treatment with CD19×CD3 bispecific single chain antibody shows a favorable toxicity profile, in contrast to conventional ALL therapies, such as chemotherapy. In light of this, the administration of the CD19×CD3 bispecific single chain antibody described herein provides a new and advantageous treatment option for acute lymphoblastic leukemia (ALL), in particular for cases in which the ALL is refractory to conventional ALL therapy, such as chemotherapy. In addition, the administration of the CD19×CD3 bispecific single chain antibody now provides for the first time for a therapy for MRD-positive ALL.

These updated results indicate that treatment of acute lymphoblastic leukemia (ALL) patients with the CD19×CD3 bispecific single chain antibody is able to convert minimal residual disease (MRD) positive acute lymphoblastic leukemia (ALL) into an MRD negative status (as exemplified by the ALL patients with immunoglobulin or TCR rearrangements, bcr/abl transcripts or t(4;11) translocations), and that this treatment is well tolerated. In light of this, the administration of the CD19×CD3 bispecific single chain antibody described herein provides an alternative treatment option especially for adult acute lymphoblastic leukemia (ALL), in particular to ALL refractory to conventional ALL therapy, such as chemotherapy and/or HSCT. Treatment with the CD19×CD3 bispecific single chain antibody is especially advantageous for the treatment of MRD-positive ALL.

The invention claimed is:

1. A method for treating acute lymphoblastic leukemia (ALL) minimal residual disease (MRD) in an adult patient in hematological remission, the method comprising
selecting the patient in hematological remission; and
administering to the patient an effective amount of a composition comprising a CD19×CD3 bispecific single chain antibody construct comprising a variable heavy chain anti-CD19 CDR1 comprising the amino acid sequence set forth in SEQ ID NO: 14, a variable heavy chain anti-CD19 CDR2 comprising the amino acid sequence set forth in SEQ ID NO: 15, a variable heavy chain anti-CD19 CDR3 comprising the amino acid sequence set forth in SEQ ID NO: 16, a variable light chain anti-CD19 CDR1 comprising the amino acid sequence set forth in SEQ ID NO: 11, a variable light chain anti-CD19 CDR2 comprising the amino acid sequence set forth in SEQ ID NO: 12, a variable light chain anti-CD19 CDR3 comprising the amino acid sequence set forth in SEQ ID NO: 13, a variable heavy chain anti-CD3 CDR1 comprising the amino acid sequence set forth in SEQ ID NO: 17, a variable heavy chain anti-CD3 CDR2 comprising the amino acid sequence set forth in SEQ ID NO: 18, a variable heavy chain anti-CD3 CDR3 comprising the amino acid sequence set forth in SEQ ID NO: 19; a variable light chain anti-CD3 CDR1 comprising the amino acid sequence set forth in SEQ ID NO: 20, a variable light chain anti-CD3 CDR2 comprising the amino acid sequence set forth in SEQ ID NO: 21, and a variable light chain anti-CD3 CDR3 comprising the amino acid sequence set forth in SEQ ID NO: 22,
wherein treatment results in stable disease or converts MRD-positive ALL into MRD-negative ALL.

2. The method of claim 1, wherein said acute lymphoblastic leukemia (ALL) is B-lineage acute lymphoblastic leukemia.

3. The method of claim 1, wherein said acute lymphoblastic leukemia (ALL) is refractory to chemotherapy.

4. The method of claim 1, further comprising administering an allogeneic hematopoietic stem cell transplantation.

5. The method of claim 1, wherein MRD is measured with quantitative detection of individual rearrangements of immunoglobulin genes or T-cell receptor (TCR) rearrangements, or by bcr/abl fusion transcripts, or by t(4;11) translocations using PCR or FACS analysis.

6. The method of claim 5, wherein the ALL patient shows a bcr/abl or a t(4;11) translocation signal above detection limit and/or at least one marker by rearrangement with a sensitivity of $\geq 10^{-4}$.

7. The method of claim 1, wherein the corresponding variable heavy chain regions ($V_H$) and the corresponding variable light chain regions ($V_L$) in said CD19×CD3 bispecific single chain antibody construct are arranged, from N-terminus to C-terminus, in the order, $V_L$(CD19)-$V_H$(CD19)-$V_H$(CD3)-$V_L$(CD3).

8. The method of claim 7, wherein said CD19×CD3 bispecific single chain antibody construct comprises the amino acid sequence set forth in SEQ ID NO: 1.

9. The method of claim 1, wherein one treatment cycle is a 4-week continuous infusion, followed by repeated cycles after a 2-week treatment-free interval.

10. The method of claim 9, wherein the treatment cycle is repeated at least three times, after determination of a MRD negative status (consolidation).

11. The method of claim 1, wherein the CD19×CD3 bispecific single chain antibody construct is to be administered in a daily dose of 10 μg to 100 μg per square meter patient body surface area.

12. The method of claim 11, wherein the CD19×CD3 bispecific single chain antibody construct is to be administered in a daily dose of 15 μg to 30 μg per square meter patient body surface area.

13. The method of claim 2, wherein said B-lineage acute lymphoblastic leukemia is B-precursor acute lymphoblastic leukemia.

14. The method of claim 7, wherein said CD19×CD3 bispecific single chain antibody construct comprises an amino acid sequence at least 90% identical to the amino acid sequence set forth in SEQ ID NO: 1.

15. The method of claim 7, wherein said CD19×CD3 bispecific single chain antibody construct comprises an amino acid sequence at least 95% identical to the amino acid sequence set forth in SEQ ID NO: 1.

16. The method of claim 9, wherein the at least four weeks of continuous infusion is followed by at least a 2-week treatment-free interval.

17. The method of claim 10, wherein each treatment cycle is followed by at least a 2-week treatment-free interval.

18. The method of claim 1, wherein the CD19×CD3 bispecific single chain antibody construct comprises a variable heavy chain anti-CD19 amino acid sequence set forth in SEQ ID NO: 3 and a variable light chain anti-CD19 amino acid sequence set forth in SEQ ID NO: 5.

19. The method of claim 1, wherein the CD19×CD3 bispecific single chain antibody construct comprises a variable heavy chain anti-CD3 amino acid sequence set forth in SEQ ID NO: 7 and a variable light chain anti-CD3 amino acid sequence set forth in SEQ ID NO: 9.

20. The method of claim 1, wherein the CD19×CD3 bispecific single chain antibody construct comprises a variable heavy chain anti-CD19 amino acid sequence set forth in SEQ ID NO: 3, a variable light chain anti-CD19 amino acid sequence set forth in SEQ ID NO: 5, a variable heavy chain anti-CD3 amino acid sequence set forth in SEQ ID NO: 7, and a variable light chain anti-CD3 amino acid sequence set forth in SEQ ID NO: 9.

21. The method of claim 1, wherein the CD19×CD3 bispecific single chain antibody construct is encoded by the nucleic acid sequence set forth in SEQ ID NO: 2.

* * * * *